(12) United States Patent
Cioanta et al.

(10) Patent No.: US 6,758,857 B2
(45) Date of Patent: Jul. 6, 2004

(54) TREATMENT CATHETERS WITH THERMALLY INSULATED REGIONS

(75) Inventors: Iulian Cioanta, Cary, NC (US); Richard Barry Klein, Cary, NC (US); Jacob Lazarovitz, Hod Hasharon (IL)

(73) Assignee: Acmi Corporation, Southborough, MA (US)

( * ) Notice: Subject to any disclaimer, the term of this patent is extended or adjusted under 35 U.S.C. 154(b) by 0 days.

(21) Appl. No.: 10/011,700

(22) Filed: Nov. 13, 2001

(65) Prior Publication Data

US 2002/0082556 A1 Jun. 27, 2002

Related U.S. Application Data

(60) Provisional application No. 60/248,109, filed on Nov. 13, 2000.

(51) Int. Cl.[7] .................................................. A61F 7/00

(52) U.S. Cl. .................. 607/105; 607/113; 607/99; 606/27; 606/192; 604/113; 604/43; 604/919; 604/101.01; 604/523; 604/544

(58) Field of Search .............................. 604/113, 114, 604/43, 96.01, 27, 48, 919, 6.13, 544, 101.01, 101.03, 101.05, 102.01, 102.02, 523, 264; 606/27, 28, 192–194; 607/104–106, 113, 116, 154, 156, 96, 99, 143

(56) References Cited

U.S. PATENT DOCUMENTS

| 4,111,865 A | * | 9/1978 | Seefried et al. ............. 521/137 |
| 4,813,429 A | | 3/1989 | Eshel et al. ................. 128/736 |
| 4,817,624 A | | 4/1989 | Newbower .................. 128/692 |

(List continued on next page.)

FOREIGN PATENT DOCUMENTS

| EP | 0599813 A2 | 8/1989 | ........... A61B/5/028 |
| EP | 0360582 A2 | 9/1989 | ........... A61B/17/36 |
| EP | 0360582 A2 | 3/1990 | |

(List continued on next page.)

OTHER PUBLICATIONS

PCT International Search Report, International Application No. PCT/US01/47793 dated Nov. 13, 2001.
Patent Cooperation Treaty, International Search Report, Jun. 13, 2002, pp. 1–5.

*Primary Examiner*—Brian L. Casler
*Assistant Examiner*—Cris Rodriguez
(74) *Attorney, Agent, or Firm*—Ganz Law, P.C.; Bradley M. Ganz, Esq.; James L. Wolfe, Esq.

(57) ABSTRACT

Flexible treatment catheters are configured to be inserted into a body lumen or cavity to deliver heated fluid through at least one fluid lumen therein to thermally treat or ablate a targeted site in a biological subject. The flexible treatment catheters can include improved thermally insulated regions comprising a mixture formed of liquid elastomeric (such as a polyurethane) mixture (which transitions to a solid state) and miniaturized hollow plastic bodies positioned between the outer wall of the treatment catheter and the fluid lumen. The thermally insulated region is configured such that, measured ex vivo, the treatment catheter can present a maximum temperature of below about 45° C. on the external surface of the outer wall of the treatment catheter when the treatment catheter circulates fluid having an inlet temperature of above or between about 60°–62° C. Alternatively or additionally, the treatment catheter can include an elongated insert positioned in a catheter fluid lumen to inhibit the closure of the lumen after exposure to fluids in the treatment catheter at temperatures sufficient to thermal ablate targeted tissue over a thermal ablation treatment period. The treatment catheter can include a urinary drainage lumen with an elongated insert frictionally engaged therewith, the drainage lumen and insert are configured to provide a fluid volume throughput through the drainage lumen of greater than about 20–25 ml/min during and after (for about 12–72 hours after) a thermal ablation session.

21 Claims, 16 Drawing Sheets

U.S. PATENT DOCUMENTS

| | | | | |
|---|---|---|---|---|
| 5,242,390 A | | 9/1993 | Goldrath | 604/55 |
| 5,257,977 A | * | 11/1993 | Eshel | 604/113 |
| 5,509,929 A | | 4/1996 | Hascoet et al. | 607/101 |
| 5,549,559 A | * | 8/1996 | Eshel | 604/113 |
| 6,042,559 A | | 3/2000 | Dobak, III | 604/7 |
| 6,134,463 A | * | 10/2000 | Wittkampf et al. | 600/374 |
| 6,166,109 A | * | 12/2000 | Spitler et al. | 523/218 |
| RE37,704 E | * | 5/2002 | Eshel | 604/113 |
| 6,682,555 B2 | * | 1/2004 | Cioanta et al. | 623/1.21 |
| 2002/0119323 A1 | * | 8/2002 | Weinert | 428/423.1 |
| 2003/0104042 A1 | * | 6/2003 | Lucast et al. | 424/449 |

FOREIGN PATENT DOCUMENTS

| | | | | |
|---|---|---|---|---|
| EP | 0417781 A1 | 9/1990 | | A61M/25/00 |
| EP | 0417781 A1 | 3/1991 | | |
| EP | 0449472 A1 | 3/1991 | | A61F/7/12 |
| EP | 0449472 A1 | 10/1991 | | |
| EP | 0599813 A2 | 6/1994 | | |

* cited by examiner

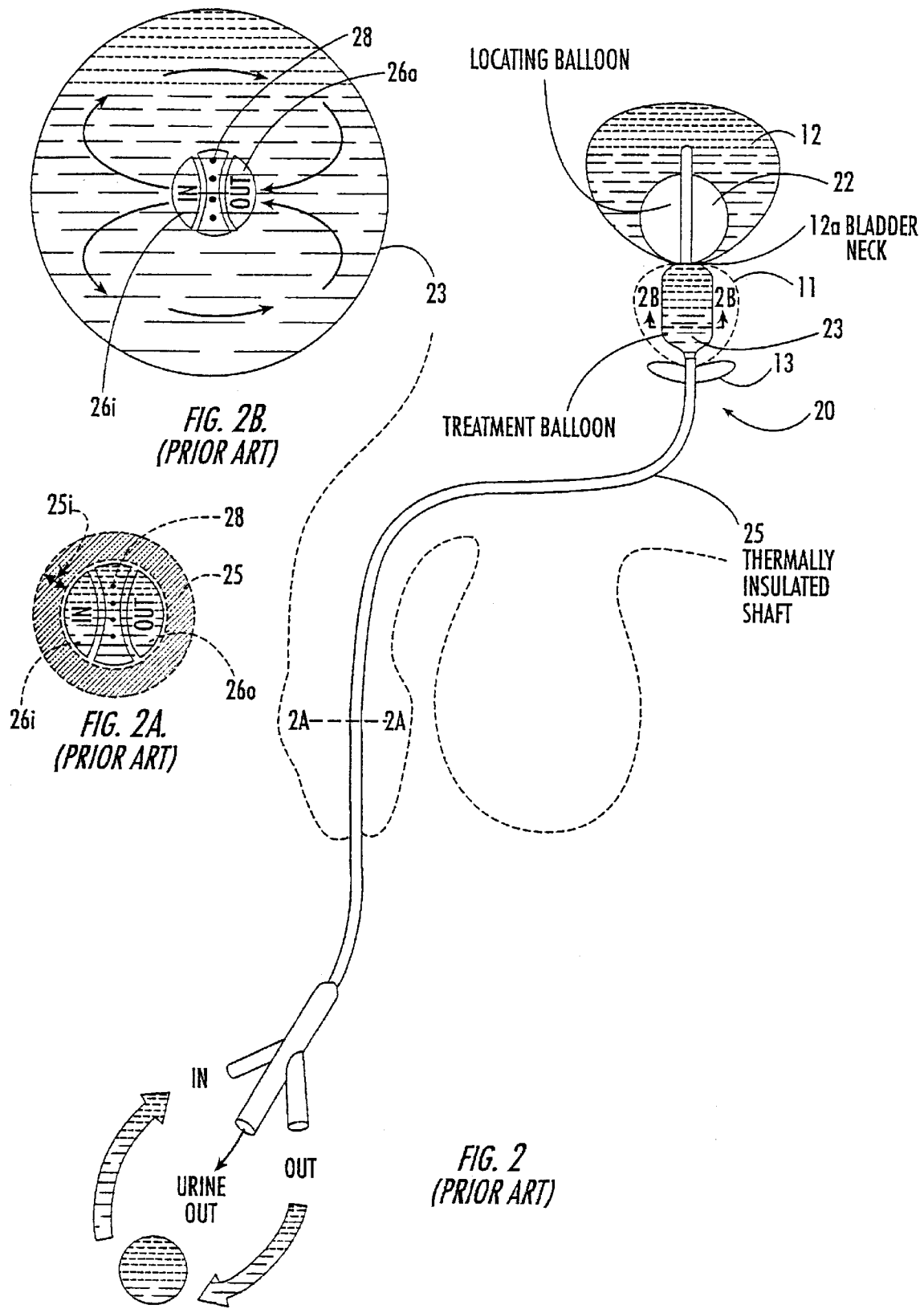

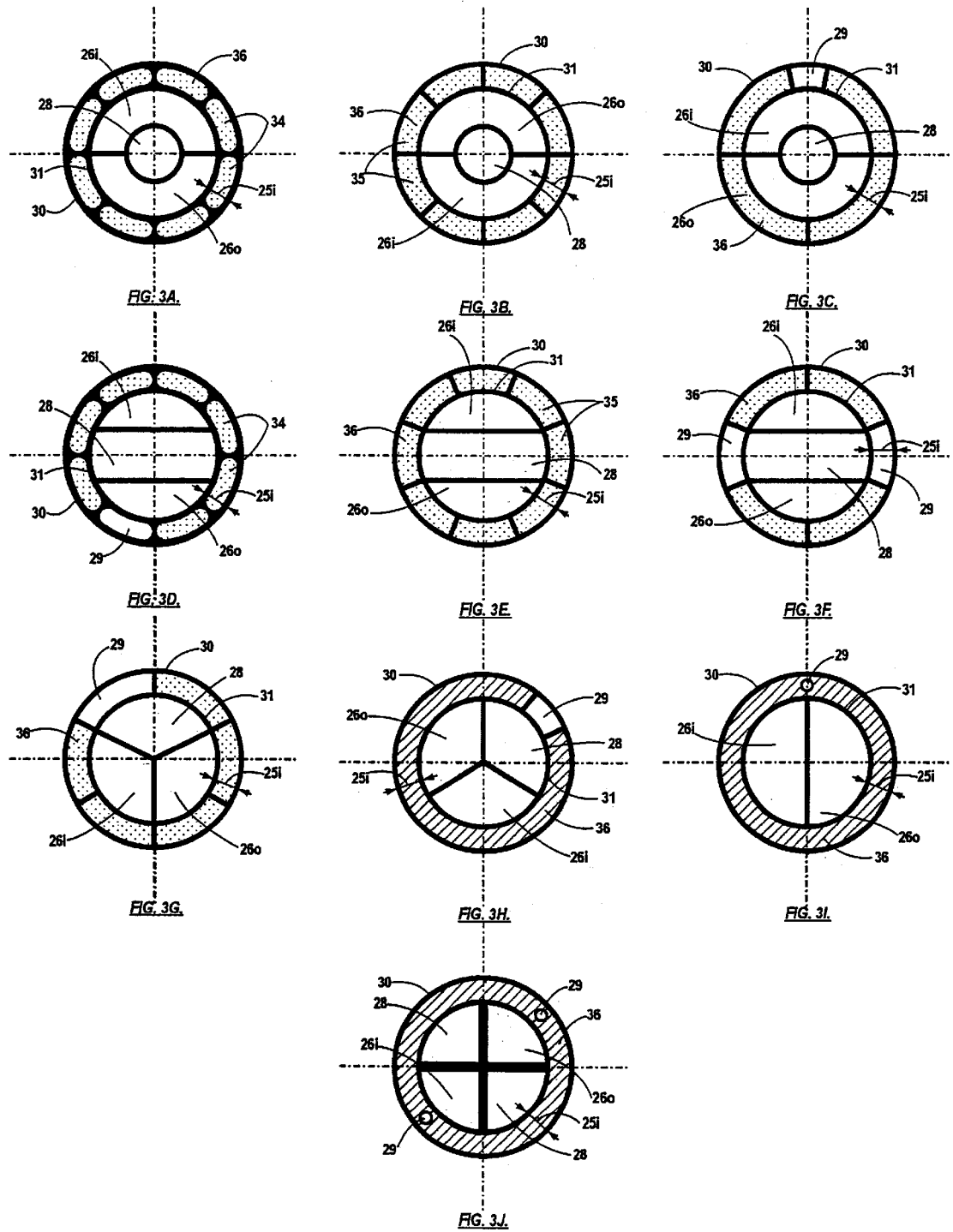

Introducing a quantity of liquid insulation mixture into a desired region of an elongated catheter, the catheter having an outerwall which is configured to encase at least one fluid lumen therein, such that the liquid insulating mixture resides intermediate the outerwall and the at least one fluid lumen.

400

Altering the physical state of the liquid mixture from a liquid flowable state to a non-liquid state to define a thermally insulated region to inhibit the thermal transfer of heat from the at least one fluid lumen through the outerwall.

```
┌─────────────────────────┐
│  Configuring and sizing a │
│  catheter such that it can be │
│  inserted into a body lumen, │
│  the catheter having at │
│  least one internal │
│  fluid channel. │
│                         │
│           500           │
└─────────────┬───────────┘
              │
┌─────────────┴───────────┐
│ Positioning an elongated insert │
│   into a selected one of the at │
│   least one fluid channel such │
│    that the insert inhibits the │
│      closure of the selected │
│       fluid channel when the │
│      catheter is held in position │
│    in the subject after exposure │
│        to thermal treatment │
│      temperatures associated │
│  with holding thermally treated │
│         fluid in the catheter. │
│                         │
│           510           │
└─────────────────────────┘
```

FIG. 15

TREATMENT CATHETERS WITH THERMALLY INSULATED REGIONS

RELATED APPLICATION

This application claims the benefit of priority from U.S. Provisional Application Serial No. 60/248,109, filed Nov. 13, 2000, the contents of which are hereby incorporated by reference as if recited in full herein.

FIELD OF THE INVENTION

The present invention relates to catheters configured for insertion into a lumen or body cavity of a subject and is particularly suitable for insertion into the male urethra.

BACKGROUND OF THE INVENTION

Conventionally, several types of thermal treatment systems have been proposed to treat certain pathologic conditions of the body by heating or thermally ablating targeted tissue. These thermal treatment systems have used various heating sources to generate the heat necessary to treat or ablate the targeted tissue. For example, laser, microwave, and radio-frequency (RF) energy sources have been proposed to produce the heat which is then directed to the targeted tissue in or around the selected body cavity. Thermal treatment systems have been used to thermally ablate prostatic tissue as well as to thermally treat or ablate the tissue of other organs, body cavities, and/or natural lumens.

One particularly successful thermal ablation system ablates the prostate by a thermocoagulation process. This thermal ablation system employs a closed loop liquid or water-induced thermotherapy (WIT) system which heats liquid, typically water, external to the body and then directs the circulating heated water into a treatment catheter. The treatment catheter is inserted through the penile meatus and held in position in the subject prior to initiation of the treatment to expose localized tissue in the prostate to ablation temperatures. The treatment catheter includes an upper end portion which, in operation, is anchored against the bladder neck and an inflatable treatment segment which is held relative to the anchored upper end portion such that it resides along the desired treatment region of the prostate. In operation, the treatment segment expands, in response to the captured circulating fluid traveling therethrough, to press against the targeted tissue in the prostate and to expose the tissue to increased temperatures associated with the circulating liquid, thereby thermally ablating the localized tissue at the treatment site. In addition, the pressurized contact can reduce the heat sink effect attributed to blood circulation in the body, thus enhancing the depth penetration of the heat transmitted by the inflatable treatment segment into the prostatic tissue.

As an acceptable alternative to surgery (transurethral resection of the prostate (TURP)), the use of WIT (water-induced thermotherapy) has been shown to be a successful and generally minimally invasive treatment of BPH (benign prostatic hyperplasia). Generally stated, the term "BPH" refers to a condition wherein the prostate gland enlarges and the prostatic tissue increases in density which can, unfortunately, tend to close off the urinary drainage path. This condition typically occurs in men as they age due to the physiological changes of the prostatic tissue (and bladder muscles) over time. To enlarge the opening in the prostate urethra (without requiring surgical incision and removal of tissue), the circulating hot water is directed through the treatment catheter which is inserted into the penile meatus up through the penile urethra and into the prostate as described above. The treatment segment expands with the hot water held therein to press the inflated treatment segment against the prostate, which then conductively heats and thermally ablates the prostatic tissue. The circulating water is typically heated to a temperature of about 60°–62° C. and the targeted tissue is thermally treated for a period of about 45 minutes to locally kill the tissue proximate the urinary drainage passage in the prostate and thereby enlarge the urinary passage through the prostate.

Subsequent to the delivery of the thermal ablation (or other) treatment, the treated tissue in the prostate undergoes a healing process. Initially, the ablated tissue can expand or swell due to inflammation or edema which can undesirably block or obstruct the prostatic urethra. Further, during the healing period, portions of the treated tissue can slough off and create an undesirable and unduly limited opening size. This post-ablation or post-therapy treatment opening size can be positively influenced by "molding" the treated or ablated tissue during the healing cycle to contour the tissue about a catheter or stent held thereat. Therefore, to facilitate proper healing and to enhance the efficacy of the therapy and particularly, ablation therapy, either the treatment catheter is left in the subject for a period of time and/or a post treatment catheter, such as a conventional Foley catheter, is positioned in the subject. Conventionally, the treatment catheter can be left in the subject for about 24–72 hours after delivering the thermal treatment to the targeted tissue to reduce the likelihood that the treatment site will be injured by premature removal of the treatment catheter.

The treatment catheter typically includes insulated regions on the proximal shaft portion of the catheter to protect non-targeted tissue from undue exposure to heat as the heated fluid travels in the catheter fluid circulation passages to the desired treatment region. The insulated regions have, in the past, been provided by configuring the catheter with an extra layer or thickness of a material along the proximal or lower shaft portion. Other treatment catheters include a series of circumferentially arranged elongated air channels or conduits which encircle the heated circulating fluid passages and provide thermal insulation along the elongated shaft portion of the catheter as described in U.S. Pat. Nos. 5,257,977 and 5,549,559 to Eshel, the contents of which are hereby incorporated by reference as if recited in full herein. As the heated fluid travels through the fluid circulating passages, the insulation reduces the heat transferred to non-targeted treatment sites, such as along the penile meatus, urethral mucosa, or urethral sphincter for the BPH application. There remains a need, nonetheless, to provide improved thermal insulation for the heated circulating fluid.

In addition, the treatment catheter is typically a relatively small, thin-walled conformable or flexible catheter that is sized to be inserted into the body lumen and which usually includes a urine drainage lumen extending through the catheter. However, the catheter can deform due to exposure to the treatment temperatures over the treatment period. This deformation can, unfortunately, partially collapse the drainage lumen and, thus, reduce the urine drainage volume capacity of the treatment catheter.

Objects and Summary of the Invention

It is therefore an object of the present invention to provide economical treatment catheters with improved thermal insulation regions.

It is another object of the present invention to provide catheters with enhanced thermal transfer or thermal transmissivity configurations in the treatment balloon region.

It is another object of the present invention to provide a device which can inhibit obstruction in a fluid path (such as to keep a urinary drainage path open), during and/or post-treatment with improved fluid flow volumes such that the subject is able to receive and/or discharge fluid at desired flow rates.

It is another object of the present invention to provide treatment catheters with increased drainage volume after exposure to elevated treatment temperatures.

It is an additional object of the present invention to provide methods for producing improved catheters with insulation and/or improved urinary drainage volumes.

It is yet another object of the present invention to provide methods for thermally treating a body lumen in a manner which inhibits the exposure of non-targeted tissue to excessive heat while allowing sufficient flow volume therethrough.

These and other objects are satisfied by the present invention, which provides, inter alia, flexible catheters with improved thermal insulation and/or improved drainage lumen configurations and related methods of forming same. The present invention can also provide methods of thermally treating a body lumen and methods of fabricating catheters with improved insulation or heat transfer capabilities.

More particularly, in one embodiment of the present invention, a treatment catheter can be configured for insertion into a body cavity or lumen of a subject. The treatment catheter comprises a flexible elongated tubular body having a thin outer wall with an external surface and at least one fluid lumen axially extending therein. The tubular body comprises a region having increased thermal insulation relative to another region thereof. The increased thermal insulation region extends a longitudinal length along the tubular body. The increased thermal insulation region includes a material configuration which provides sufficient thermal insulation between the at least one fluid lumen and the external surface to inhibit thermal ablation of non-targeted tissue during thermal ablation treatments.

In certain embodiments, the thermal insulation is configured to provide a temperature gradient between the temperature of the circulating fluid (which for thermal ablation procedures can be heated to about 60°–62° C.) in the at least one fluid lumen and the external surface of the outer wall of the tubular body which is greater than about 15 degrees when measured in vitro or ex vivo. That is, the inner temperature is greater than that at the external wall outer surface. The thermal insulation can be configured to be in communication with and attached to the outer wall of the tubular body so as to provide sufficient tensile strength to allow for insertion and removal from the subject without impeding the function of the catheter.

The thermal insulation material layer can comprise a mixture of an elastomeric, rubber or polymeric material and hollow microspheres (which can be small or miniaturized hollow plastic bodies sized on the order of $\mu$m). The voids provided by the hollow microspheres in the insulation layer can provide a thermal conductivity path across the integrated material layer which is interrupted to thereby provide improved thermal insulation (which impedes thermal conductivity) across the width of the material insulating layer. In certain embodiments, the polymer material is polyurethane and the in operation thermal insulation material layer can provide an increased thermal temperature gradient across the width of the material mixture layer which is greater than the same thickness of the elastomeric material alone. The improved temperature gradient can be about 10–14% greater compared to that of the temperature gradient of the same thickness of the elastomeric material alone. Further, unlike other porous materials, the microspheres, when combined with a desired polymer or elastomeric material according to embodiments of the present invention, can provide good mechanical strength between the outer wall of the catheter on one side and the outer wall of an inner lumen(s) on the other, which may not be available with other materials comprising voids (this structure can help improve the tensile strength therebetween).

The increased insulation region may be configured such that, in operation, heated circulating liquid is directed through the treatment catheter and, as it enters the tubular body, is heated to a temperature of at about at least 60° C. and, when measured ex vivo, the external surface of the outer wall about the increased thermal insulation region exhibits a maximum temperature of about 42–45° C. during or after a thermal treatment period of at least about 5–30 minutes.

In other embodiments, the treatment catheter can be configured with increased thermal transmissivity about the expandable treatment balloon. The increased thermal transmissivity can be provided by forming the expandable balloon wall from a suitable compound including an elastomeric substrate material such as polyurethane mixed with ceramic microspheres. The increased thermal transmissivity catheter can also include biocompatible coatings over the exterior surface of a portion of the catheter.

The present invention can provide treatment catheters configured for insertion into a body cavity or lumen of a subject which includes: (a) a flexible elongated tubular body having a thin outer wall with an external surface; (b) at least one fluid lumen axially extending within the tubular body such that the at least one lumen is encased by the outer wall; and (c) an elongated insert sized and configured to be received into the at least one fluid lumen to inhibit the closure of the fluid lumen to allow fluid throughput volumes of at least about 20 ml/min after exposure to thermal treatment temperatures during a thermal treatment session.

The thermal treatment session can expose the fluid lumen and insert to temperatures above about 45° C. during a thermal ablation procedure. In certain embodiments, the fluid lumen is exposed to fluid in the range of about 50°–62° C. or greater during a treatment session, which can last for at least about 5–30 minutes, and up to about 45 minutes or more, as the application demands.

In certain embodiments, the insert can be formed from a low friction material (for easy insertion into the desired fluid lumen) and/or a material which resists thermal deformation after exposure to thermal ablation temperatures and/or which is sufficiently rigid so as to retain a desired opening size for the fluid flow in the fluid lumen even when exposed in situ to compressive pressures from swollen tissue or edema. The insert can be formed from a fluoropolymer such as polytetrafluoroethylene (PTFE) having a hardness of about Shore A 98 such as Teflon, or tetrafluoroethylene (TFE), fluorinated ethylene-propylene (FEP), perfluoroalkoxy (PFA), ethylene tetrafluoroethylene (ETFE), or polyvinylidene fluoride (PVDF), and the like.

For embodiments of the catheters having a plurality of inner lumens such as an inlet channel, and outlet channel and the fluid lumen, the insert can be configured to maintain the desired fluid opening size in the fluid lumen even when the insert is exposed to increased pressures from the quantity of fluid held captured and circulating in the inlet and outlet channels about the fluid lumen.

Preferably, the insert is configured such that, after exposure to a thermal therapy including, but not limited to a thermal ablation therapy session, it allows fluid volumes of at least about 20–25 ml/min. In one embodiment, the thin outer wall is formed from polyvinylchloride (PVC) or polyurethane. The drainage lumen with the insert can be configured to allow fluid throughput volumes of above about 25 ml/min after exposure to a maximum circulating fluid temperature therein of at least about 40°–62° C. even after exposure to these conditions for a period of about at least 40 minutes.

In one embodiment, the at least one fluid lumen is a plurality of axially extending fluid lumens and the treatment catheter further includes an inflatable treatment balloon positioned about a peripheral distal portion of the elongated tubular body. The treatment balloon is in fluid communication with at least one of the plurality of fluid lumens such that the treatment balloon is expandable to a configuration which extends outwardly a distance from the outer wall of the tubular body. The catheter may also include a thin inner tubular wall spaced apart from the thin tubular outer wall and a plurality of elongated insulation channels axially extending therebetween. The plurality of fluid lumens can include a circulating fluid inlet lumen, a circulating fluid outlet lumen, and a drainage and fluid delivery lumen. Preferably, an elongated insert is disposed in at least the drainage and fluid delivery lumen. One or more of the plurality of elongated insulation channels can be configured to encase a quantity of non-gaseous insulation material comprising polyurethane disposed therein to define an insulated region along a proximal portion of said tubular body intermediate the fluid lumens and the outer wall.

Yet another aspect of the present invention is a method of thermally treating a target region in the body. The method comprises the steps of (a) inserting a treatment catheter into a body lumen; (b) heating liquid external of the subject to above about 45°–60° C.; (c) circulating the heated liquid in the treatment catheter such that it travels, captured in the treatment catheter, to a target treatment region; (d) exposing the tissue in the targeted region to a temperature of above about 45° C. for a predetermined thermal ablation treatment period corresponding to the heated liquid in the circulating step; (e) insulating non-targeted tissue below the targeted region such that the non-targeted tissue is exposed to a maximum temperature of about 42–45° C. from contact with the treatment catheter during the circulating step; (f) terminating the circulation of the heated liquid after the thermal ablation treatment period; (g) leaving the treatment catheter in the subject after the terminating step for an initial healing period of from about 12–72 hours; (h) directing body fluids to drain through the treatment catheter during the circulating, exposing, and leaving steps, wherein the treatment catheter is configured in a manner which allows a drainage volume of above about 20 ml/min (and more preferably above about 25 ml/min) after the circulating and exposing steps; and (i) removing the treatment catheter after the initial healing period.

The method can be used to treat urinary or prostate conditions such as BPH. In certain embodiments, the circulating liquid can be heated to above or about 60–62° C. external of the subject and directed into the treatment catheter at an inlet temperature of about 60–62°C. The treatment catheter can also include a flexible drainage lumen with an elongated insert disposed therein, the elongated insert is configured to inhibit the closure of the drainage lumen and to facilitate increased urine or other body fluids drainage flow rates (or flow rates of drugs, treatment rinses, or other liquids into the body) after the exposing and circulating steps.

An additional aspect of the present invention is a method of inhibiting the closure of a flexible thin walled lumen in a catheter configured for insertion into a lumen or cavity of a biological subject. The method comprises the steps of (a) configuring a flexible elongated catheter such that it is sized for insertion into a natural body lumen or cavity of a biological subject and such that it can bend to follow the contour of the body lumen or cavity, the flexible catheter comprising at least one fluid channel therein; and (b) positioning an elongated insert into the at least one fluid channel such that it axially extends along a length thereof, the elongated insert is configured to maintain an open fluid channel during and after the flexible catheter delivers a thermal therapy to a desired target site in the biological subject.

Another aspect of the present invention is a method for providing increased thermal insulation in a treatment catheter having at least one fluid lumen therein. The treatment catheter has an outer wall which encases the at least one fluid lumen. The treatment catheter is configured to deliver thermal treatment to a target site in a natural lumen or body cavity of a biological subject. The thermal treatment can include one or more of cooling, heating, or thermal ablation treatments. The method comprises the steps of: (a) introducing a quantity of liquid insulation mixture into a desired region of the treatment catheter such that it is held intermediate the at least one fluid lumen and the outer surface of the treatment catheter; and (b) altering the physical state of the liquid mixture from liquid to a non-liquid state (or from a flowable to a non-flowing state) to define a thermally insulated region in the catheter.

In one embodiment, the treatment catheter has an elongated tubular body, and the treatment catheter further comprises a plurality of axially extending insulation lumens circumferentially arranged to encase the at least one fluid lumen below the outer wall. In this embodiment, the increased thermal insulation is carried out in the introducing step by inserting (which can include flowably injecting) the liquid insulation mixture into one or more of the plurality of insulation lumens.

In certain embodiments, the liquid insulation mixture can comprise liquid polyurethane or a liquid insulation mixture comprising initially liquid polyurethane and hollow plastic microspheres.

In some embodiments, the treatment catheters can be provided as a set of prostatic treatment catheters, each configured for insertion into the male urethra (such as for treating BPH). However, the set is provided such that each treatment balloon which expands to deliver the thermal treatment is sized a different length to allow customized fit to a particular subject (the treatment balloon which is adapted to reside in a portion of the prostatic urethra which can vary patient to patient and the catheter treatment balloon itself can be provided in lengths ranging from about 2–6 cm, typically in increments of about ½ cm).

Advantageously, the present invention provides flexible treatment catheters. The present invention allows, for applications which employ body fluid drainage lumens (or drug delivery or other fluids), increased rigidity about the drainage or delivery lumen which can be used to provide improved throughput volumes (increased drainage volumes therethrough) in the subject even after the catheter is exposed to elevated temperatures during thermal ablation or thermal therapy treatments.

In summary, certain embodiments of the present invention the treatment catheters can include increased thermally insulated regions compared to conventional catheters. The increased thermally insulated regions are preferably formed with selected insulative materials inserted or positioned intermediate the external wall of the catheter and the internal fluid passageways or lumens about a length of the catheter shaft which resides in the subject during treatment to inhibit non-targeted tissue from being exposed to thermal treatment temperatures. Thus, the treatment catheters of the instant invention can protect the non-targeted tissue from undesirable exposure to thermal temperatures directed to the targeted tissue during delivery of the thermal treatment. Related methods for forming the insulation in the treatment catheters such as by injecting a flowable microsphere solution into desired regions of the catheter and then solidifying to define improved insulation regions are also described.

Certain embodiments of the present invention additionally, or alternatively, provide treatment catheters which are configured to allow improved drainage and/or flow rates for other fluids such as flushing liquids to be directed into the subject therethrough. Certain of the embodiments described are particularly suitable for a subject undergoing thermal therapy or thermal ablation treatment to a localized target region in a natural body cavity or lumen such as within the prostatic urethra. The treatment catheter can remain in position for an initial portion of the healing process (temporally proximate to the post thermal ablation treatment) and can be used to deliver medicaments or rinses to the treatment region during the healing process (which in prostate treatments can promote healing and/or inhibit UTI). The treatment catheter can include one or a combination of suitable coatings such as hydrophilic coatings which can help the ease of insertion into the body cavity, antimicrobial coatings, anti-inflammatory coatings, anti-scarring coatings, and antibiotic coatings. In addition, the catheter can be used to deliver suitable fluids to the treated region to help facilitate healing and/or reduce the likelihood of infection.

BRIEF DESCRIPTION OF THE DRAWINGS

The accompanying drawings, which are incorporated in and constitute a part of the specification, illustrate embodiments of the invention and, together with the description, serve to explain principles of the invention. A portion of the disclosure of this patent document contains material which is subject to copyright protection. The copyright owner has no objection to the reproduction by anyone of the patent document or the patent disclosure, as it appears in the Patent and Trademark Office patent file or records, but otherwise reserves all rights whatsoever.

FIG. 2 is a schematic illustration of the prostate portion of the male urethra illustrating a prior art treatment catheter in position in a subject for delivery of thermal ablation treatment.

FIGS. 2A and 2B are enlarged section views of the prior art treatment catheter shown in FIG. 2.

FIG. 14 is a block diagram of a method for fabricating a catheter with insulated regions according to embodiments of the present invention.

FIG. 15 is a block diagram of a method for inhibiting the closure of a fluid channel according to embodiments of the present invention.

DETAILED DESCRIPTION OF EMBODIMENTS OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the figures, certain elements, regions, or features may be exaggerated for clarity. Like numbers refer to like elements throughout. In the figures, broken lines indicate that the associated operation or feature is optional.

Figure 1:
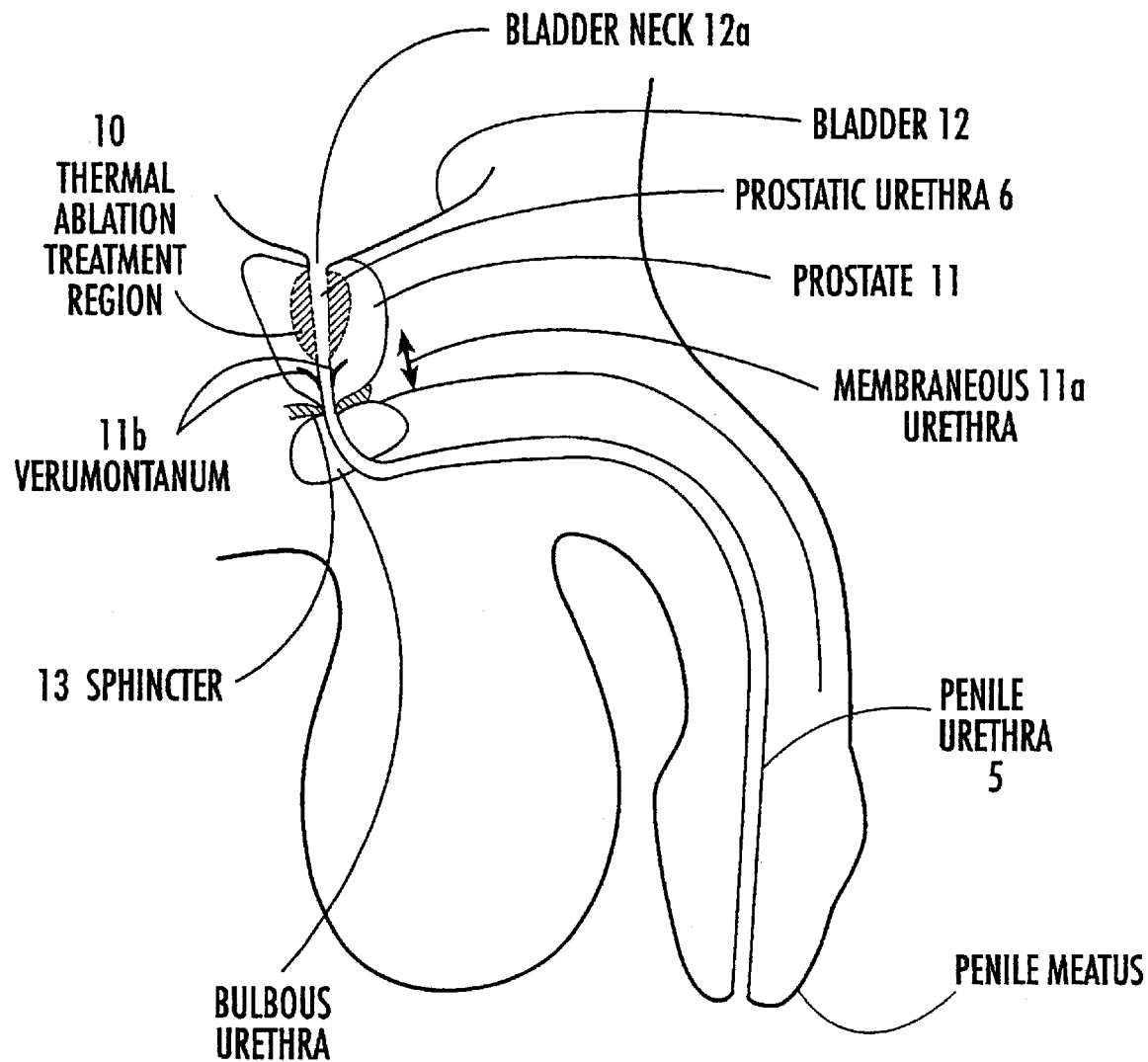
FIG. 1 is a schematic illustration of the anatomy of the male urethra showing a thermal ablation treatment region in the prostate.

Referring now to FIG. 1, the thermal ablation treatment region 10 is indicated by the lined region in the prostate 11. The term "thermal ablation" refers to exposing the targeted tissue to a temperature which is sufficient to kill the tissue. The thermal ablation can be carried out in a number of ways. As shown in FIG. 2, in certain embodiments, the thermal ablation is carried out by causing the targeted tissue to thermocoagulate via contact with an expandable treatment balloon 23 on a catheter 20 inserted into the subject which is configured to direct circulating hot liquid heated external of the body of the subject to the targeted treatment region within the biological subject.

In certain embodiments related to thermal ablation therapies, the targeted tissue is exposed to an elevated temperature which is greater than or equal to about 45° C. for a predetermined period of time. In other embodiments, the treatment catheters may be used for other thermal therapies such as to deliver cooled liquids (cooled to temperatures below the average body temperature such as to about 15–20° C. or even to cryogenic temperatures) or to deliver heated liquids (heated to temperatures below about 45° C.) to a target region in the cavity or natural lumen in the subject's body. The present invention finds use for both veterinary and medical applications. The present invention may be advantageously employed for treatment of subjects, in particular human subjects. Subjects, according to the present invention, includes animal subjects, and are preferably mammalian subjects (e.g., humans, canines, felines, bovines, caprines, ovines, equines, rodents, porcines, and/or lagomorphs), and more preferably are human subjects.

For ease of discussion, the embodiments of the present invention will be primarily discussed for use in the male urethra. However, the catheters of the present invention may be alternately configured and adapted as appropriate for insertion in other natural lumens or body cavities such as, but not limited to, the colon, the uterus, the cervix, the throat, mouth or other respiratory passages, the ear, the nose, blood vessels, and the like.

In certain embodiments, the treatment catheter can be used to administer a treatment to the prostate to treat prostatitis, cancer, and/or BPH. In particular embodiments, thermal ablation therapy can be used to treat BPH. In treating BPH, it is also preferred that the prostatic tissue is thermally treated by contact with an expandable treatment balloon which expands responsive to the heated fluid captured and/or circulating therein. The heat can be generated by a microwave, RF, ultrasound, and the like locally at the treatment site or can be generated external of the body. For example, in certain embodiments circulating systems are employed and the liquid is held such that it is captured in the treatment catheter and delivered to the treatment balloon to cause the treatment balloon to expand with heated liquid. The liquid can thus be heated external of the subject (outside the body of the subject) and then introduced to the catheter. In certain embodiments, such as but not limited to, for BPH thermal ablation treatments, the circulating heated fluid can be introduced into the catheter at a temperature of about 60°–62° C. for a treatment period which is at least 30 minutes, and in particular embodiments for at least about 42–45 minutes, in duration.

In other embodiments, such as for treating prostatitis, a thermal internal massage treatment can be administered by repetitively pulsing the expansion and contraction of a treatment balloon on the catheter (as it resides inside the body) for selected time periods. The duration of the treatment may not include the initial time to reach the desired treatment temperature (or the time to decrease therefrom post-treatment). For example, heating the fluid to about 40–47° C. such that the prostatic tissue is exposed to non-ablation or low-level ablation temperatures for a major portion (or all) of the treatment session. In other embodiments, the fluid can be heated to an elevated level (about 50–62° C. for an initial portion of the treatment) and then reduced for the remainder of the treatment session to between about 40–47° C., and typically to about 45–47° C. See co-pending, co-assigned U.S. Provisional Application Ser. No. 60/308,344 for additional description of thermal massage therapies, the contents of which are hereby incorporated by reference as if recited in full herein.

For certain embodiments, such as prostatitis and/or BPH thermal ablation therapy, the treatment can be targeted to be carried out in a localized treatment region within the urethra from the prostate, the treatment region 10 being generally described as including the upper portion of the urethra (termed the "prostatic urethra") so as to extend generally below the bladder neck 12a and above the verumontanum 11b of the subject. Alternatively, the treatment region 10 may include the bladder neck 12a or a portion of the bladder neck itself.

It is noted that the circulating heated fluid for thermal ablation treatments can be heated to temperatures above about 45° C. and delivered to the targeted tissue to provide the thermal ablation temperatures for different applications for different lengths of treatment as the desired application dictates. For example, the liquid can be heated to a temperature of at least about 50° C. and then circulated (as heated liquid) into a catheter that is positioned in the desired location in the subject so as to expose the targeted tissue to the heated temperature for from about 5–30 minutes or more.

In certain embodiments, once the thermal ablation therapy has been delivered to the subject, the treatment catheter 20 is left in position in the subject for an initial recovery period. Preferably, this initial recovery period is from about 12–72 hours, and more preferably about 24–48 hours. Leaving the treatment catheter in position for this initial period can reduce bleeding and subsequent blood clotting upon immediate post-treatment removal thereof. A suitable thermal treatment system and treatment catheters are available from ArgoMed, Inc. located in Cary, N.C. See also, U.S. Pat. Nos. 5,257,977 and 5,549,559 to Eshel, and co-assigned U.S. patent application Ser. No. 09/433,952 to Eshel et al, the contents of which are hereby incorporated by reference as if recited in full herein.

FIG. 2 illustrates a conventional prior art treatment catheter 20 used in a water induced thermotherapy prostate treatment system identified as the Thermoflex® System available from ArgoMed Inc. of Cary, N. C. As shown, the treatment catheter 20 includes an anchoring balloon 22, a treatment balloon 23, and an elongated shaft 25. As shown in FIGS. 2A and 2B, the catheter 20 also includes inlet and outlet fluid circulating paths 26i, 26o, respectively, as well as a urinary drainage channel 28 (which can also be used to deliver medicaments therethrough while the catheter 20 is in position in the subject). The anchoring balloon 22 can be in fluid communication with the treatment balloon 23, such that both are inflatable by the circulating heated fluid or, as shown in FIG. 2, can be in fluid isolation from the treatment balloon 23 (inflatable by an air channel directed thereto). Preferably, the upper anchoring balloon 22 is separately inflatable to allow this balloon 22 to be inflated before the treatment balloon 23. This can reduce the likelihood that the upper anchoring balloon 22 will be inflated below the desired location (potentially introducing damage to the bladder neck 12a or the upper portion of the prostate urethra) and facilitate proper positioning of the catheter 20 in the prostate relative to the bladder. As shown, the anchoring balloon 22 extends a distance into the bladder that may hold a quantity of urine 12.

In operation, heated fluid, which can be water or a water-based liquid, is heated external of the subject, directed into the catheter 20, and circulated in the enclosed fluid paths 26i, 26o in the catheter 20. The fluid is directed through the shaft 25 via the inlet path 26i to the treatment balloon 23 located proximate the desired treatment site, out of the treatment balloon 23 to the outlet path 26o, and out of the subject. As shown in FIG. 2B, the circulating fluid is directed into the treatment balloon 23 which then expands in response to the quantity of fluid held therein. Preferably, a low volume of circulating heated fluid is physically circulated, during operation, at any one time, through a closed loop system to deliver the thermal ablation treatment via the treatment catheter 20. The term "low volume" means below about 100 ml. In particular embodiments, the low volume system can be configured to circulate between about 20–50 ml.

In operation, in order to anchor the catheter 20 in a desired position or location within the prostate 11 (after the catheter 20 is inserted into the prostate 11) the anchoring balloon 22 is inflated via a fluid introduced through the shaft 25 to the distal portion of the catheter 20 to cause the anchoring balloon 22 to take on an expanded configuration and reside against the bladder neck of the subject. Thus, when expanded, the anchoring balloon 22 is adapted to position the treatment balloon 23 in the prostate relative to the bladder. When deflated, the catheter 20 (including the anchoring and treatment balloons 22, 23) is preferably configured as a smooth, substantially constant profile member to allow for ease of insertion into the body (the balloons may substantially collapse against the central body or shaft of the catheter).

The circulating fluid (and the anchoring balloon inflation media, when separately inflatable) is preferably selected to be non-toxic and to reduce any potential noxious effect to the subject should a situation arise where the balloon integrity may be compromised, accidentally rupture, leak, or otherwise become impaired during service.

The catheter 20 is preferably flexibly configured so as to be able to bend and flex to follow the shape of the lumen or cavity (even those with curvatures as shown in FIG. 2) as it is introduced into the lumen or cavity until a distal portion of the catheter 20 reaches the desired treatment site.

The catheter 20 can be sized as an elongated tubular body with a relatively small cross-sectional area having a thin outer wall so as to be able to be inserted into and extend along a length of the desired lumen to reach the desired treatment site. As used herein, the term "thin outer wall" means a wall having a thickness of about 2 mm or less, and preferably about 1.2 mm or less, and can be, in certain embodiments about 0.5 mm or less. For prostate or male urinary applications, the cross-sectional width or outer diameter of the catheter 20 about the tubular body is typically between about 6–8 mm (18–24 French). Of course, as noted above, the flexible catheter 20 can be alternatively sized and dimensioned to fit other lumens, cavities and/or treatment applications.

In a preferred embodiment, a major portion of the cross-sectional area of the shaft region 25 of the catheter 20 is taken up by the size of the fluid channel, or channels, held therein. In certain embodiments, such as but not limited to those directed to prostate or male urinary applications, the catheter 20 includes at least three separate fluid channels, the circulating inlet and outlet channels 26i, 26o and the fluid drainage and/or medicament delivery channel 28 in the shaft region 25 (FIG. 2) as shown in FIGS. 2A, 3A–3T and 4A–4F. Therefore, as also shown in these figures, the insulation region 25i is typically physically limited to a predetermined length of the tubular body and is also configured so as to laterally extend within a small outer region of the shaft 25 encasing the intermediately-held fluid channels 26i, 26o, 28, as will be discussed further below.

The flexible catheter 20 can also be configured such that it is sufficiently rigid to be able to maintain an opening in the drainage lumen 28 when inserted and in position in situ (and exposed to compressive swelling pressures or edema in the localized treatment region after a therapy session or treatment) sufficient to provide at least about 50% of the cross-sectional area, and preferably at least about 75%–90% or more, of the cross-sectional area, of the drainage lumen 28 relative to the pre-insertion catheter 28 size. As such, the catheter 20 can be flexibly configured such that it is sufficiently conformable to yield to the contours of the subject's body as it is inserted therethrough and into position in the desired region of the subject, yet sufficiently rigid to provide an open drainage lumen when it resides in position, in the body (such as in the prostate), and exposed to tissue which is exhibiting distress during or subsequent to undergoing a therapy or thermal treatment.

In certain embodiments, the catheter 20 can be configured such that it is able to maintain a sufficiently sized drainage opening in the drainage lumen 28 to allow desired flow volumes therethrough when exposed to compressive pressures from the treated tissue on the order of about 7–21 psi after exposure to elevated temperatures above about 40° C. for at least about 10 minutes, and typically above about 45° C. for above about 30 minutes. The catheters 20 of the instant invention can also be used to maintain an open passage of desired size for other treatments or applications where there is a desire to maintain the open passage in a flexible catheter which is exposed to edema or stress in the subject.

Figure 3K:
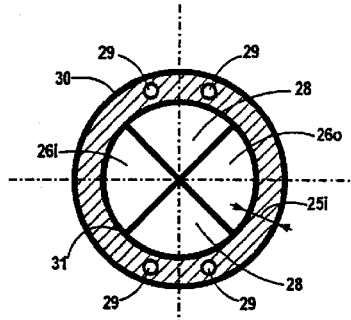
FIGS. 3A–3T are enlarged cross-sectional views of embodiments of a catheter shaft having insulated regions with exemplary lumen configurations according to the present invention.
Figure 3L:
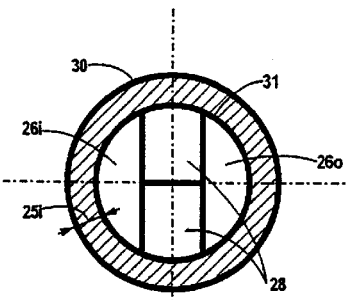
Figure 3M:
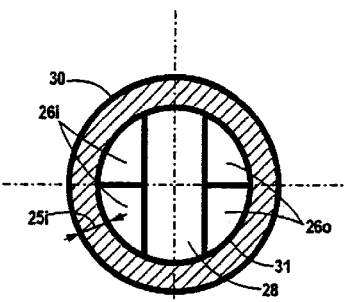
Figure 3N:
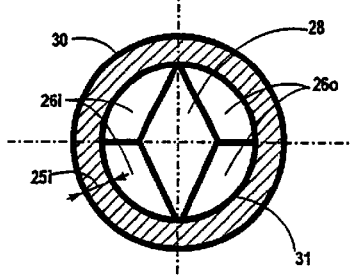
Figure 3O:
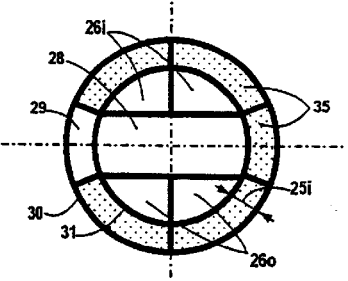
Figure 3P:
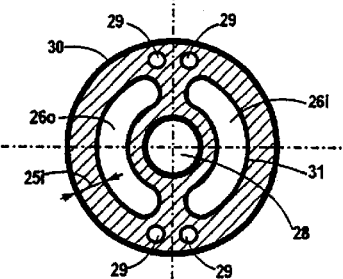

As shown in FIG. 2, the elongated shaft 25 has increased thermal insulation 25i at least along the length which resides below or away from the targeted treatment region (for prostate treatments, this is the region in the male urethra below the prostate) during the thermal therapy to reduce the likelihood that the non-targeted tissue will be exposed to undue (cooling, elevated, or ablation) temperatures. FIGS. 3A–3T illustrate embodiments of the shaft region 25 of the treatment catheter 20 showing increased thermal insulation configurations (i.e., increased relative to the region of the treatment balloon 23) according to the present invention. FIGS. 4A–4G illustrate cross-sectional views of additional embodiments of thermal insulation 25i and lumen configurations in the shaft region 25. Certain embodiments of the catheter cross-sectional profile or perimeter shapes shown in FIGS. 3 and 4 include a plurality of partitions or segments forming a part of the insulated shaft region 25i. The plurality of segments are located between the outer wall and the circulating fluid lumens. The plurality of segments can define discrete enclosed void spaces. Each of the void spaces also have perimeter shapes, typically oval, circular, or curvilinear, or polygonal such as in the shape of a triangle, square, rectangle, parallelogram, trapezoid, and the like. The insulation region can include more than one void space shape. The void spaces may be filled (or partially filled) with fluid such as air, gas, liquid, gelatinous, or solid or semi-solid materials. The void space(s) may be used to drain fluid therein and/or to direct inflation media to the anchoring balloon and the like.

As shown in FIG. 3A, the catheter shaft 25 can include an outer wall 30, an inner wall 31, and a plurality of conduits 34 circumferentially arranged (preferably in close proximity and/or abutting contact) intermediate the inner and outer walls 31, 30, respectively. A plurality of internal fluid passages are encased by the inner wall 31. As shown, the internal fluid passages include three separate passages, the circulating inlet and outlet paths 26i, 26o, and the centrally disposed drainage lumen 28. The inlet and outlet paths 26i, 26o are annularly arranged around (substantially concentrically aligned with) the centrally located drainage channel 28. As is also shown, the conduits 34 can be filled with a quantity of a selected (non-gaseous) insulation media, material, or material mixture 36 to provide enhanced thermal insulation for the shaft 25. Exemplary embodiments of selected insulation materials will be discussed further below. Thus, the outer wall 30, the inner wall 31, and the plurality of conduits 34 filled with the selected insulating material 36 together define the thermal insulation 25i for the lower portion of the shaft 25.

FIG. 3B illustrates embodiments with a similar configuration to that of FIG. 3A with the internal fluid lumens 26i, 26o, and 28, arranged as in FIG. 3A. This embodiment includes a plurality of partitioned segments 35 which are circumferentially arranged to radially extend between the outer wall 30 and the inner wall 31. Selected ones or all of the partitioned segments 35 can be filled with a quantity of a selected insulation material 36. The insulation material 36 can be formed of a compound material mixture comprising hollow microspheres as will be discussed further below.

FIG. 3C again illustrates insulation embodiments with a similar configuration to that of FIG. 3A with the internal fluid lumens 26i, 26o, and 28, arranged as in FIG. 3A and at least one axially extending void space 29 that can be configured in the catheter. In certain embodiments the void space 29 can act as an inflation passage 29 that is provided in the insulation layer 36 such that it extends along a desired length of the catheter 20. In other embodiments, the void space 29 can be used to direct fluid or medicaments to desired regions in the body. In other embodiments, the catheter can include separate void spaces for each of these functions. For ease of discussion, the void space 29 will be primarily described as an inflation passage hereafter.

The number of inflation passages 29 can vary depending on the application (other numbers are shown in the embodiments of FIG. 3). The inflation passage is in fluid communication with an inflation source which is externally located (outside the subject) on one end and in fluid communication with an inflatable balloon segment (such as the bladder anchoring or locating balloon 22 shown in FIG. 2) on the other end.

FIGS. 3D, 3E, and 3F are similar to FIGS. 3A, 3B, and 3C, respectively, but illustrate a different internal fluid lumen arrangement for the inlet outlet circulation and fluid drainage channels or passages 26i, 26o and 28. In these embodiments, the lumens themselves are arranged similar to the arrangement shown in FIG. 2A. FIGS. 3D–3F illustrate that the increased insulation region 25i can include tubes or passages 34, 35 filled with a selected insulation material or material mixture 36.

The insulation material 36 can be deposited, sprayed, injected, or otherwise layered on the inner wall or positioned in the void spaces defined between the inner and outer walls of the catheter 31, 30, respectively. As shown in certain of the figures, the outer wall 30 and inner wall 31 are thin wall elongated (axially extending) tubes that are separated by an intermediate material layer comprising the selected insulation material 36. In other embodiments, such as shown in FIG. 3H, the outer wall 30 can be sized to surround the inner wall 31 and a quantity of insulation material can be positioned therebetween, and may be configured to provide a void space or axially extending channel 29 as desired.

Alternatively, such as shown in FIGS. 3I, and 3J, the outer wall 30 can be defined by a single material layer formed directly onto the inner wall 31 with a sufficient lateral thickness. The outer wall and underlying layer can be configured from a material comprising the selected insulation material 36. In certain embodiments, the thickness of the insulating material layer across the outer wall surface to the inner surface thereof can be about 1.2 mm. A small conduit can be formed into the thickness of the layer or a channel can be formed to define the inflation passage 29 as desired.

The catheter embodiment of FIG. 3I is similar to the embodiments of FIGS. 3C and 3F, but includes only two inner fluid flow lumens. For circulating systems, it is preferred that, as shown, the catheter 20 includes at least one inlet and outlet channel 26i, 26o. This embodiment illustrates that, for some applications, drainage lumens 28 may not be desired and/or necessary. In other embodiments, separate circulating paths may not be necessary, so a catheter may also be configured with only one lumen (not shown) or use the two lumens for other purposes.

FIGS. 3G and 3H illustrate embodiments of catheters which can include three inner fluid flow lumens, the inlet outlet circulation and fluid drainage channels or passages 26i, 26o, and 28 arranged with radially extending segments all converging from the inner wall 31 to a common center.

Figure 3Q:
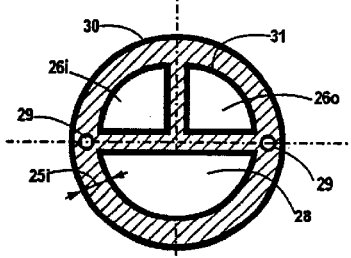
Figure 3R:
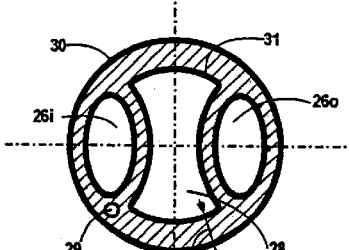
Figure 3S:
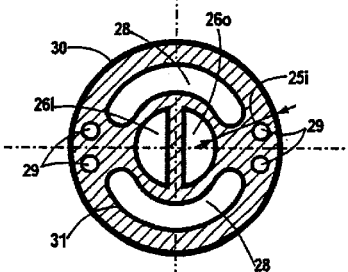
Figure 3T:
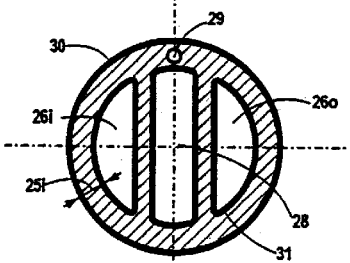

FIGS. 3P, 3Q, 3R and 3T also illustrate the use of three fluid lumens 26i, 26o, and 28. FIG. 3Q illustrates an oval cross-sectional profile and also shows that the lumens are offset from the center of the tubular body such that the drainage channel 28 is spaced more closely to the outer wall 30 than the fluid inlet and outlet circulating lumens 26i, 26o. FIG. 3Q also shows that the drainage channel 28 has a semi-circular shape extending across a major portion of the width of the tubular body. The drainage channel 28 can have a diameter which is on the order of greater than or equal to the sum of both the widths of the inlet and outlet circulating lumens 26i, 26o. FIG. 3T illustrates an increased thickness of material to separate the drainage channel 28 from the circulation channels 26i, 26o over the configuration shown in FIG. 3F.

FIGS. 3J, 3K, 3L, and 3S illustrate catheter embodiments which can have four inner fluid flow lumens. FIGS. 3J, 3K, 3L and 3S illustrate catheters which have one inlet and one outlet circulation channel 26i, 26o, and two fluid drainage channels 28. FIGS. 3J and 3K illustrate that the drainage channels 28 are positioned in the catheter so as to be diametrically opposed from each other. FIG. 3K also illustrates the use of four inflation passages 29. FIG. 3S illustrates that the two drainage channels 28 are located intermediate the outer wall 30 and the inlet and outlet paths 26i, 26o. As shown, the drainage channels 28 can be annularly arranged around the two opposing and substantially centrally located inlet and outlet paths 26i, 26o.

FIGS. 3M, 3N, and 3O illustrate catheter embodiments which can have five inner fluid flow lumens. As shown, the circulating channels 26i, 26o each include two passages which may be in fluid communication or may be in fluid isolation and which direct the treatment fluid to or from the treatment balloon 23. FIG. 3N illustrates a diamond shaped drainage passage 28, while FIG. 3M illustrates a rectangular shaped passage 28. As is also shown, the drainage channels 28 can be centrally disposed within the catheter tubular body. In other embodiments, such as shown in FIGS. 3K, 3Q, and 3S, the drainage channel 28 is offset with respect to the center of the catheter.

For brevity, not all combinations of suitable wall structures and lumen arrangements have been illustrated herein. It is noted that each of the exemplary lumen arrangements shown in the figures can be formed with any of the desired insulation or wall structures of the present invention. For example, each of the lumen configurations may be combined with a desired insulation such as a selected material layer 36, partitioned segments 35 (or segments 125 FIGS. 4A–G, as will be described further below), and tubular channels 34 (whether filled with air or another gas or a selected non-gaseous insulation material composition).

FIGS. 4A–4G illustrate additional embodiments of catheter body insulation regions 25i or structures with various lumen arrangements. In certain embodiments, the present invention can also provide segments with spaces which are oriented and shaped to reduce the amount of contact area between the internal lumen and/or the outer wall and/or to provide increased lateral or radial rigidity to inhibit closure of the internal lumen(s). In operation, the segments are configured so that they can provide increased thermal resistivity and/or decrease the radially transmitted thermal conduction and may also provide increased structural rigidity. That is, the perimeter shapes and orientation of one or more of the segments can provide point contact for localized regions proximate the heated or cooled fluid in the internal lumen or lumens and/or the outer wall. The configurations can thereby provide a reduced heat conduction surface area at points circumferentially arranged about the shaft.

In certain embodiments, the perimeter shape of the segment spaces 125 (FIGS. 4A–4G) can include at least one edge portion or corner. One or more of the segment space 125 perimeter shapes can be oriented between the inner wall 31 (or the internal fluid lumen or lumens) and the outer wall 30 such that the perimeter shape radially tapers into the edge portion or corner either toward one or the other, or both, such that the edge portion is the forwardmost part of the segment at either the outer wall or the inner wall. Thus, the shape and orientation of the segment defines a point contact for the proximately located inner lumen or outer wall. As used herein, the term "point contact" can include a localized contact region rather than merely a sharp corner or pin point of contact, as shown, for example, in FIGS. 4A–4G.

Figure 4A:
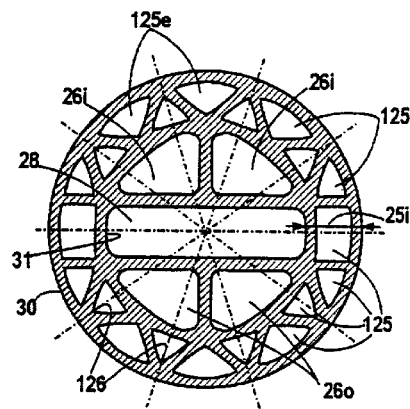
FIGS. 4A–4F are enlarged cross sectional views of additional embodiments of catheter shafts having insulated regions and exemplary lumen configurations according to the present invention.
Figure 4B:
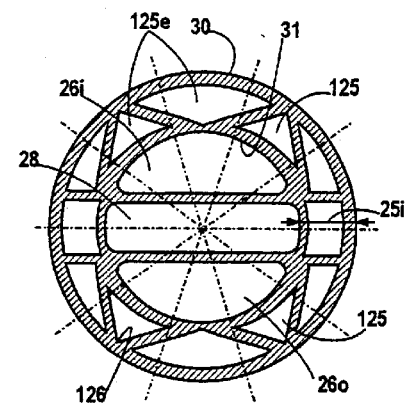
Figure 4C:
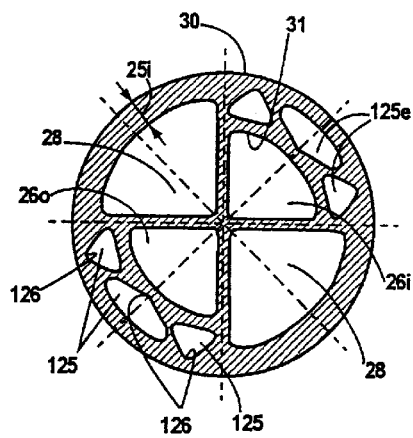
Figure 4D:
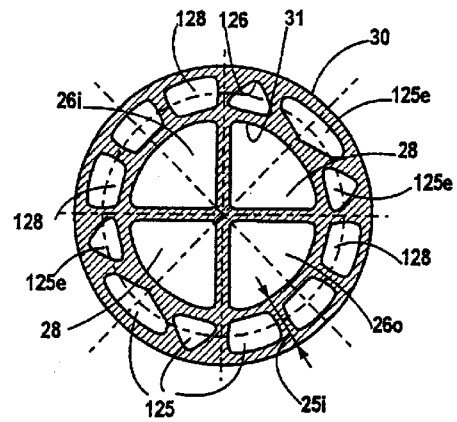
Figure 4E:
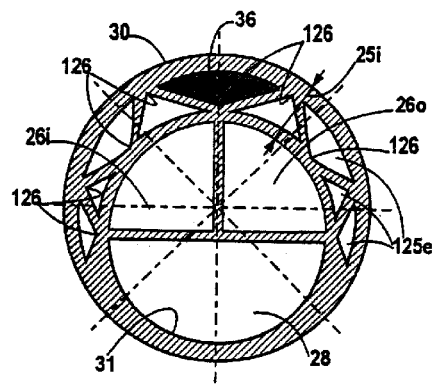
Figure 4F:
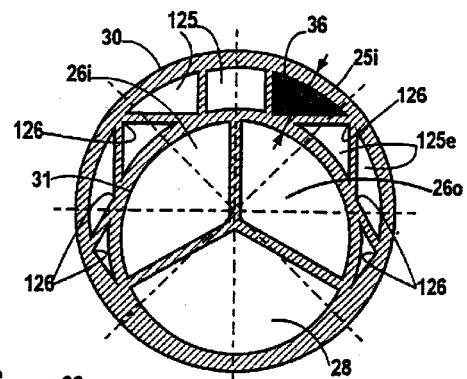
Figure 4G:
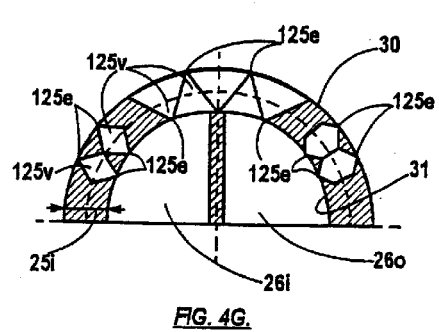
FIG. 4G is an enlarged partial cross-sectional view of still other embodiments of catheter shafts with insulated regions according to the present invention.

Looking, for example, at FIG. 4G, when viewed in cross-section, the segments 125 define void spaces 125v with perimeters of different shapes, preferably shapes having corners or edge portions 125e. For example, polygonal shapes such as, but not limited to, substantially triangular, square, rectangular, trapezoidal, pentagonal, hexagonal, parallelogram, and the like. The void spaces 125v are positioned between the internal lumen, or as shown, lumens 26i, 26o, and the outer wall 30. The void spaces or segments 125 are oriented such that at least one corner or edge portion 125e contacts or is more proximate (e.g., extends such that it is closer to either the internal wall 31 (or outer surface of the walls of the internal lumens 25i, 25o) or the outer wall 30 than the rest of the perimeter of the void space. This segment configuration can reduce the amount contact surface between either the outer wall 30 and the segment 125 or the inner wall 31 and the segment 125. FIG. 4G illustrates several examples of suitable configurations such as a square oriented as a diamond shape (providing point contact with each the inner and outer walls), a triangle shape with one edge (pointing to the inner wall 31), and a hexagon. The catheter can be configured with one or more of these segment configurations.

FIGS. 4A–4G illustrate embodiments where the wall structure of the catheter at least in the insulation region 25i employs at least one segment 125 having at least one substantially triangulated or protruding edge portion 126. As described above, in operation, it is expected that the reduced contact surface area either or both at the outer wall 30 or the inner wall 31 about the circulating fluid inlet and outlet paths 26i, 26o may provide improved thermal insulation and/or improved structural rigidity so as to inhibit undue deformation attributed to circulating heated fluid through the flexible catheter circulating fluid inlet and outlet paths 26i, 26o to the treatment balloon during thermal treatments such as near thermal ablation temperatures and/or at or above thermal ablation temperatures that can last up to about 40–42 minutes, or longer, during some treatments. FIGS. 4A–4G illustrate different configurations and quantities of inner lumens.

FIGS. 4A and 4B illustrate embodiments where a plurality of segments 125 can be positioned intermediate the outer wall 30 and the inner wall 31 about both the circulating fluid inlet and outlet paths 26i, 26o. The segments 125 may be all arranged so that the pointed or protruding edge portion 126 is positioned to face or contact the outer wall 30 and/or face the inner wall 31. In FIGS. 4A and 4B, the drainage lumen 28 is centrally disposed and two laterally opposing end segments can be positioned intermediate the outer wall 30 and the drainage lumen 28 as desired.

FIGS. 4C and 4D illustrate embodiments where the catheter can include a plurality of segments 125 of differing sizes and configurations positioned intermediate the outer wall 31 and the circulating fluid inlet and outlet paths 26i, 26o. In addition, the segments can be arranged such that some of the triangulated edge portions 126 face the outer wall 30 while others face the inner wall 31. As is also shown, the tubular body of the catheter shaft proximate the two diametrically opposed drainage channels 28 may be formed of a layer of a selected material without segments 125 (FIG. 4C) and/or with different shaped segments 128 as shown in FIGS. 4C and 4D. In addition, the drainage lumen can be configured as a plurality of separate lumens (shown as two diametrically opposed lumens). Catheters configured similar to the embodiments of FIGS. 4A–4G may increase fluid volumes allowed to flow through the drainage channels 28 by about 60% over conventional configurations.

FIGS. 4E and 4F illustrate embodiments where the fluid flow lumen, the circulating fluid inlet and outlet channels 26*i*, 26*o* and the drainage channel 28 (and/or fluid delivery channel), can be offset from the axially extending center axis of the tubular body (the center of the tubular body is indicated by the dotted line axis drawn in the figure). FIG. 4E illustrates embodiments where the drainage channel 28 can have a width which is about the size of the sum of the widths of the adjacent regions of the circulating fluid inlet and outlet channels 26*i*, 26*o*. As is also shown, the drainage channel 28 can be shaped as a half-circle and the circulating fluid inlet and outlet channels 26*i*, 26*o* can be shaped as quarter-circles (all can be radially aligned with a substantially common center). FIG. 4F illustrates embodiments where the three fluid flow channels 26*i*, 26*o*, 28 can be substantially equally sized and configured. As shown, a central lumen can be subdivided into three wedge shapes. The three lumens can be divided so that each fluid flow lumen extends from a common center and such that each lumen has about ⅓ the area enclosed by the inner wall 31 or so that the drainage channel 28 has an increased area relative to the inlet and outlet circulating fluid channels 26*i*, 26*o*. The cross-sectional perimeter shape of the catheter shown in FIGS. 4A–4G is substantially circular, however, the present invention is not limited thereto and may include other shapes, such as, but not limited to, oval, polygonal or otherwise. FIGS. 4E and 4F also illustrate that a selected insulation material 36 (gaseous or non-gaseous) can also be positioned in one or more of the void spaces defined by the segments 125.

In certain embodiments, the segments 125 can also be radially arranged to extend about a subset of the circumference of the tubular body including the region of the shaft outer wall 30 adjacent the circulating fluid inlet and outlet channels 26*i*, 26*o*. The segments 125 can be arranged to taper off in size such that they have the largest dimensions at the location opposing the drainage channel and then (gradually) reduce in size as the position on the shaft approaches the drainage channel 28. The segments 125 can terminate proximate the region overlying the drainage channel 28. The drainage channel 28 can be separated by a thickness of a material layer without an intermediate baffles or segments, as typically, the drainage channel 28 is not used to deliver excessively heated or cooled fluids. The segments 125 can be configured to define voids spaces or can be filled with a selected insulation material such as gases, liquids, solids, or other desired media.

In certain embodiments, the selected insulation material 36 can comprise polyurethane. The polyurethane can be provided as a single layer thickness for at least a portion of the outer wall to form insulation along the shaft (such as shown for the single layer embodiment of FIG. 3H and the portion of the shaft adjacent the drainage channel in 4E). Alternatively, a flowable insulation material can be flowably inserted between the inner and outer walls (such as inserted into the void spaces defined by partitions 35 (FIG. 3B), tubes 34 (FIG. 3A) or segments 125 (FIGS. 4A–4F). The flowable insulation can be liquid (wholly or partially), gelatinous, or foam. In certain embodiments the flowable insulation material can include liquid polyurethane which is subsequently hardened or solidified.

In additional embodiments, the selected insulation material can comprise a suitable substrate material such as polyurethane mixed with hollow plastic, elastomeric, polymer, or copolymer microspheres sized in a range of about 5–100 μm (typically averaging about 50 μm). Suitable hollow microspheres are identified as 551-DE available from Expancel located in Duluth, Ga. The insulation mixture can comprise at least about 10% volume of microspheres. In certain embodiments, the insulation mixture is formulated to have a volumetric ratio of between about 2:1–15:1, and preferably a ratio of between about 3:1–5:1, volume of liquid polyurethane to microspheres. Other miniaturized (sized in the range of about 10–500 μm) hollow elastomeric, plastic, polymer, or copolymer shapes or bodies can also be used according to the present invention.

In addition, other suitable elastomeric or flexible substrate materials (other than polyurethane) can also be used. For example, to form the outer and/or inner walls 30, 31, a quantity of microspheres and materials, such as, but not limited to, polymers, copolymers, polyesters, nylon, and urethanes, can be used. These materials can include polyurethane, silicone, latex, epoxy, rubber, polyvinylchloride (PVC), polyolefins such as polyethylene terephthalate (PET), polyethylene (PE), polypropylene (PP), PTFE, polyamide, polycarbonate, or other suitable biomedically-acceptable elastomers.

Figure 8:
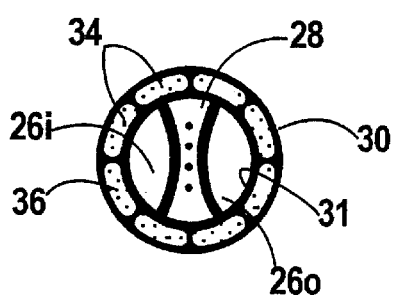
FIG. 8 is an enlarged section view of an embodiment of an insulated shaft region taken along line 8—8 in FIG. 7.

In certain embodiments, as shown in FIG. 8, the catheter 20 can include an outer wall 30 and an inner wall 31 each having a thickness of about 0.2–0.5 mm formed of a thermoplastic elastomer. In certain embodiments, selected portions or components of the catheter 20 may also include ceramic, glass, stainless steel or other suitable biomedically acceptable materials (not shown) to help form connections between lumens or walls or between circulating passages or heating components and the like, or to provide increased or decreased thermal resistivity or to inhibit closure of the drainage lumen.

As also shown in FIG. 8, a plurality of tubes or conduits 34 are positioned between the two walls 30, 31. The tubes 34 have a width (or pre-compressed diameter) of about 0.5–0.8 mm that may be compressed after insertion by the contact with the opposing walls 30, 31. Of course the tubes 34 (or indeed the inner wall 31) can include, but need not have, a curvilinear profile or elongated curved edge cross-section and can be alternately configured. The tubes 34 can also be replaced with or incorporated with partitions 35 or segments 125 such as are shown in FIGS. 3B and 4A, respectively.

The insulation mixture may be introduced into the treatment catheter 20 by dispersing a quantity of an insulation mixture 36 comprising a liquid or flowable material (which can be polyurethane with hollow plastic microspheres) into the desired region of the catheter, such as the smaller tubes 34 (the quantity will vary depending on the length of the conduit corresponding to the length of the shaft 25). After a period of time (such as 12–24 hours), or exposure to a heat or light source, the liquid will solidify, harden, or cure into a solid. A syringe or other injection or liquid and/or flow delivery system can be used to direct the liquid mixture into the tubes 34. Additional quantities of the liquid insulation may be inserted external of the tubes 34 between the walls 30, 31.

Figure 9:
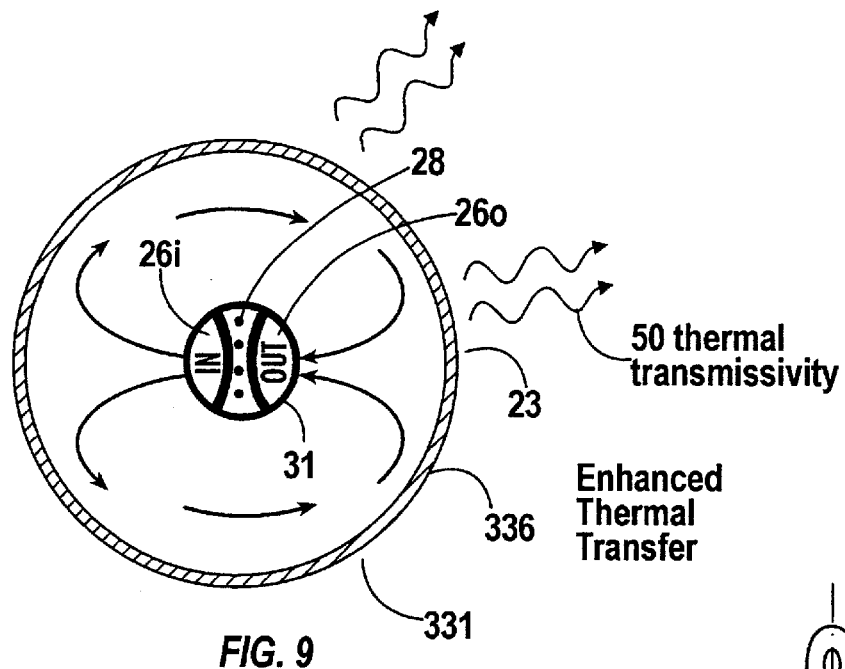
FIG. 9 is a greatly enlarged section view of a treatment balloon region of a catheter taken along line 9—9 in FIG. 7.

In another embodiment, as illustrated by FIG. 9, the treatment balloon 23 can include an expandable/collapsible thin outer wall 331 formed of an elastomeric material such as those described above, including, for example, polyurethane, nylon, polyethylene, or PVC (which is typically plasticized so that the material is sufficiently elastic and flexibly expandable) which also comprises ceramic or silica microspheres 336 to enhance the thermal transmissivity 50 of the treatment balloon 23. The mixture can comprise at least about 10% volume of ceramic microspheres. The ceramic or silica microspheres can be hollow and sized in the range of about 106–350 μm. In certain embodiments, the mixture is formulated to have a volumetric ratio of between about 2:1–15:1, and preferably a ratio of between about 3:1–5:1, volume of elastomeric material to microspheres that can be layered onto one or more of the surfaces of the balloon (such as the outer surface) to enhance the heat transfer properties thereof. Other miniaturized (typically sized in the range of about 10–750 μm) bodies that may also be hollow, can also be used according to the present invention. The ceramic or silica microspheres can be integrated into the wall material or applied as a thin film coating onto the inner or outer surface of the outer wall or inner wall 30, 31. Suitable ceramic hollow microspheres sized with average ranges of about 106 and 350 μm are available from CHL Microspheres, Inc., located in Helenwood, Tenn.

Figure 10:
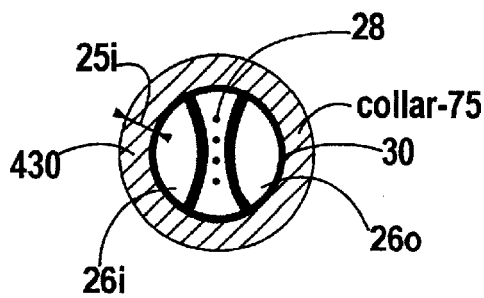
FIG. 10 is an enlarged section view of a distal portion of a catheter taken along line 10—10 of FIG. 7.
Figure 7:
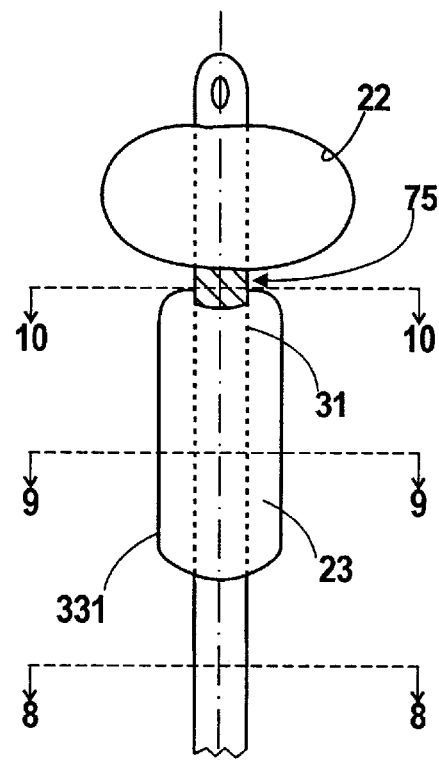
FIG. 7 is a schematic partial cutaway view of a catheter according to an embodiment of the present invention.

As shown in FIGS. 7 and 10, the catheter 20 may also comprise a thermal insulation collar 75 providing increased thermal insulation 430 for this region of the catheter. The collar 75 can be provided as an additional layer of insulating material of a selected material, preferably comprising polyurethane or nylon, located at a distal portion of the catheter 20 (above the distal end portion of the treatment balloon 23 and below or adjacent the anchoring balloon 22) or as a separate thermally insulating component which can be positioned onto and/or attached to the outer wall 30 of the catheter 20 at the desired location.

Figure 11A:
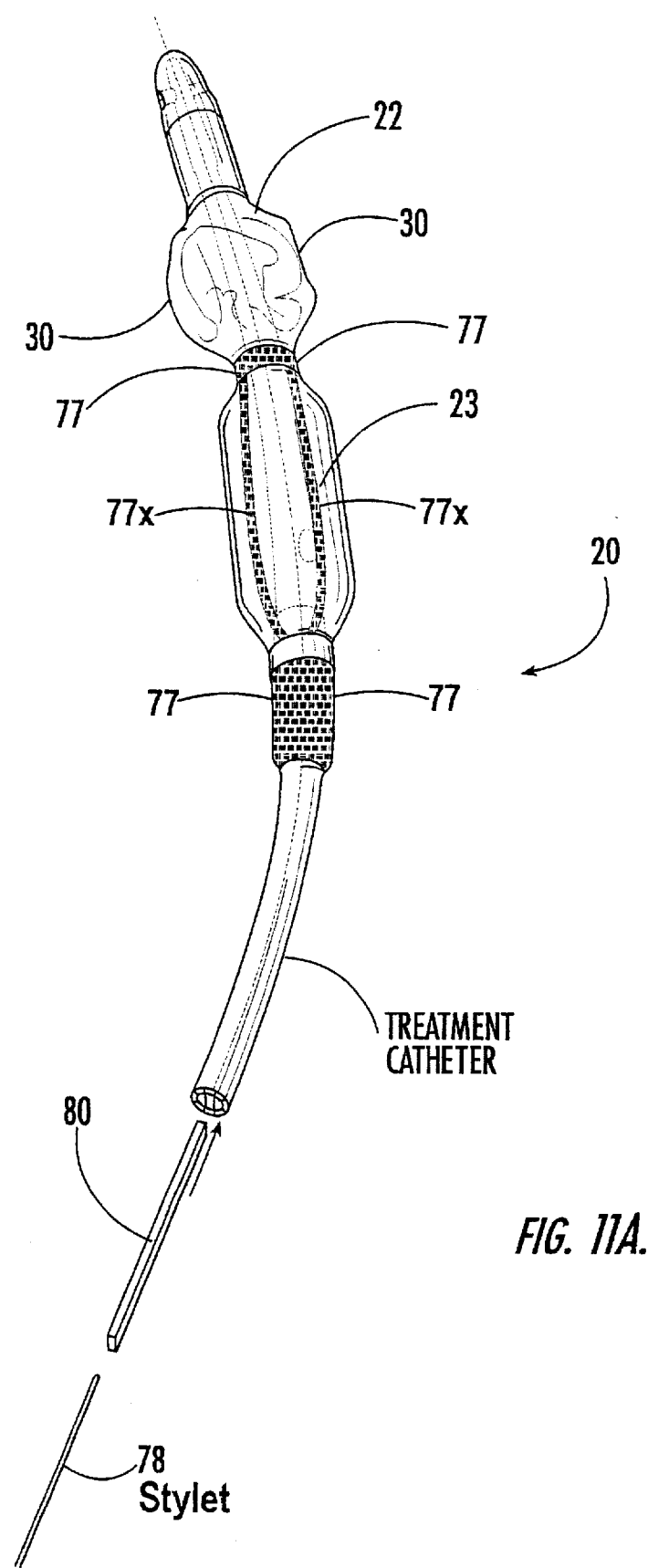
FIG. 11A is a partial exploded view of a treatment catheter according to embodiments of the present invention.

Turning now to FIG. 11A, another aspect of the present invention is shown. As illustrated, an elongated insert 80 is sized and configured to be received into the urinary drainage lumen 28 of the treatment catheter 20. The insert 80, in position in the drainage lumen 28, extends along the catheter 20 substantially coextensively with the fluid circulating lumens 26i, 26o. In another embodiment, the insert 80 can extend beyond the treatment balloon 23 and circulating lumens 26i, 26o (to a location proximate the urinary discharge port—see FIG. 2). In still other embodiments, the insert can be positioned in the drainage channel or lumen 28 such that it terminates adjacent to or before the treatment balloon heated fluid lumens and/or which is located outside the subject during operation. The insert 80 can be configured and sized to correspond substantially with the opening size of the drainage lumen 28 such that it can be insertably positioned into and held frictionally engaged against the inner surface of the drainage lumen 28. The insert 80 resides in the drainage lumen 28 and provides structural rigidity and integrity so as to inhibit closure in the drainage lumen 28, thereby promoting increased urinary drainage volume during and after exposure to temperatures associated with thermal ablation treatments as well as to withstand pressures associated with contact with the treated tissues of the subject. The insert 80 can be sufficiently rigid to be able to maintain a desired opening size in the drainage lumen 28 when inserted and in position in situ (and exposed to compressive swelling pressures or edema in the localized treatment region after a therapy session or treatment) sufficient to provide at least about 50% of the cross-sectional area, and preferably at least about 75%–90% or more, of the pre-insertion size of the cross-sectional area of the drainage lumen 28.

Figure 11B:
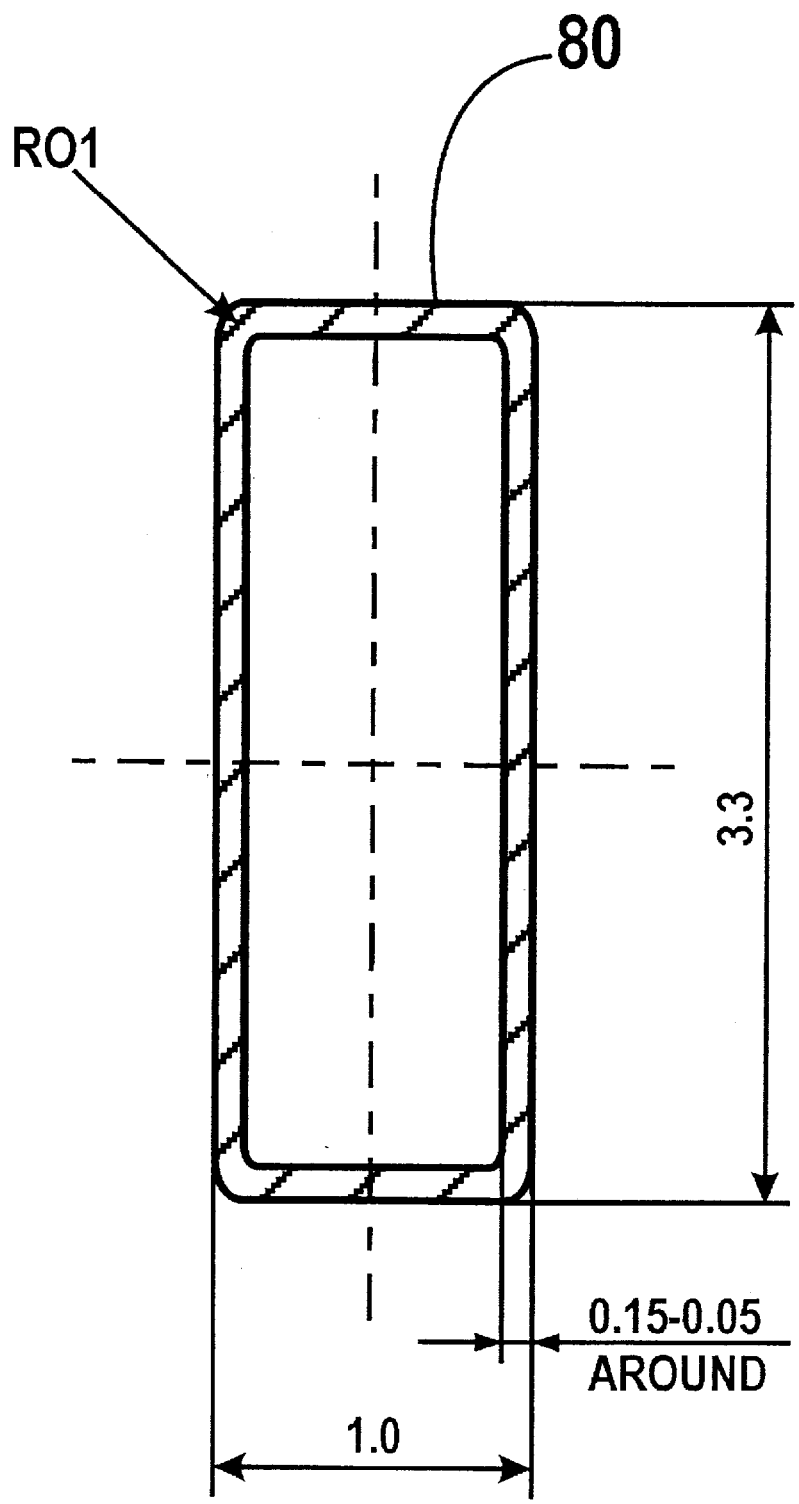
FIG. 11B is a greatly enlarged end view of an insert according to embodiments of the present invention.

As shown in FIG. 11B, the insert 80 can be a rectangular shaped tube having a wall thickness of about 0.15 mm and a cross-section width and length which is about 3.3 mm×1.0 mm. The insert can extend a major distance or all of the length of the shaft from the treatment balloon (and above) to a location outside the body. In particular embodiments, the insert 80 can be about 370–390 mm long. In certain embodiments, the insert 80 can be formed of PTFE (polytetrafluoroethylene). Of course, other materials and insert shapes (the cross-sectional shapes can include, but are not limited to, ovals, half-circles, squares, hexagons, pentagons, parallelograms, ellipses, and the like) can also be used as long as the insert 80 is able to provide sufficient structural rigidity to inhibit closure after and during exposure to thermal treatments. In certain embodiments, the insert 80 can be configured so as to inhibit closure and/or maintain a desired opening size when exposed to thermal treatments (such as at about 40–45° C. or higher) or thermal ablation temperatures for a period of over 5–10 minutes. In certain embodiments, the treatment can have a duration of about 30–40 minutes and the thermal treatment temperature can be between about 50–80° C. for at least a portion of the treatment.

Although illustrated as a continuous length, the insert 80 can be provided as a plurality of discrete segments which are serially insertable into the catheter or which can be attached by conduits or strings so that the segments can be abuttedly positioned or spaced apart as desired along the desired length of the catheter (not shown).

It will be appreciated by those of skill in the art that guides or pushers can be used to insert and position the flexible catheter 20 in the prostate. For example, guide wire or stylet placement systems are well known. Guide wires are typically used with a catheter having an open end while stylets are used with catheters having closed ends or tips to inhibit the stylet from contacting the urethra and potentially causing injury thereto. In addition, although the closed end configurations of the catheter 20 shown herein have been illustrated as substantially upright, they can also be curved into other configurations such as Coude or Tiemen. To assemble the insert 80 (FIG. 11A) to the catheter 20, a conventional stylet 78 (typically a thin round cross-sectional profile metallic guiding member) can be directed or introduced into the insert 80 (typically a friction or snug fit) which together are then inserted into the catheter 20 drainage lumen 28 until the insert 80 reaches the desired distal location.

Figure 11C:
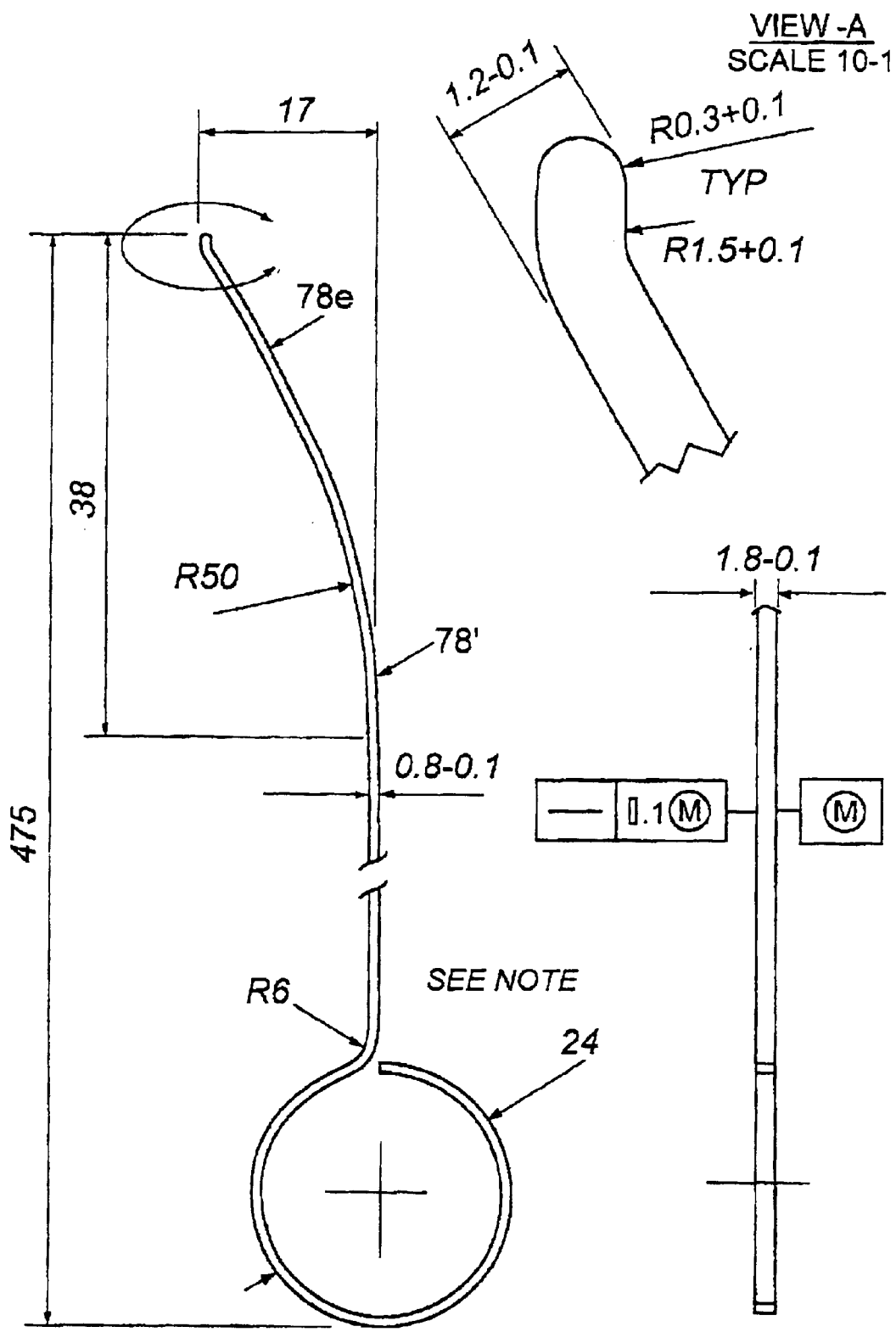
FIG. 11C is a front view of a stylet suitable for positioning the insert of FIG. 11B according to one embodiment of the present invention.

Alternatively, a stylet 78 can be shaped and sized to correspond to the shape of the insert 80 and/or drainage lumen 28. As shown in FIG. 11C, the stylet 78' is a thin flat cross-sectional profile sized and configured to slidably mate with the inner dimensions of a rectangular insert 80. As is also shown, the stylet 78' includes a Tiemen end 78e. The stylet 78, 78' can then be slidably removed, leaving the insert 80 in position in the drainage lumen 28. Other insertion guides can also be used and, if reduced slightly from a size associated with conventional stylets, can facilitate ease of assembly into the insert 80.

Figure 12A:
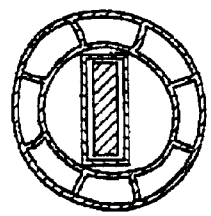
FIGS. 12A–12D are views of cross-sections of a catheter according to one embodiment of the present invention with a PTFE insert positioned in the urine drainage canal after exposure to WIT input temperatures (60°–62° C.) circulated in the catheter and insert for about 40 minutes or more.
Figure 12B:
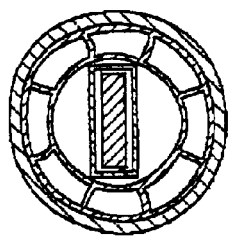
Figure 12C:
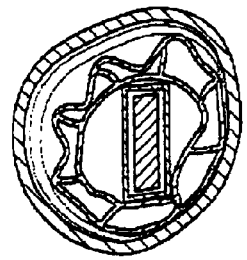
Figure 12D:
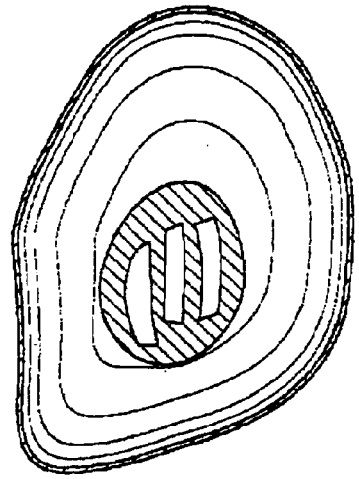

FIGS. 12A–12D are cross-sectional views of a catheter with an insert 80 positioned in the drainage lumen 28 according to the present invention. The views were taken along sequential positions about the length of a conventional catheter 20 configured as shown in FIG. 2 (and modified with the insert 80), from a more proximal shaft portion associated with FIG. 12A to a position inside the treatment balloon segment of the catheter associated with FIG. 12D. The views were taken after the catheter 20 had experienced a conventional prostatic thermal ablation procedure (the fluid having a fluid inlet temperature into the catheter of about 62° C.). As shown in FIG. 12C, the catheter 20, in the region proximate the treatment balloon 23, can experience plastic deformation due to fluid pressure and/or temperatures associated with the circulating heated fluid. The functioning of the peristaltic pump was not affected during thermal ablation treatment with the insert 80 in position (the flow per minute was substantially the same as in a conventional catheter).

Figure 13:
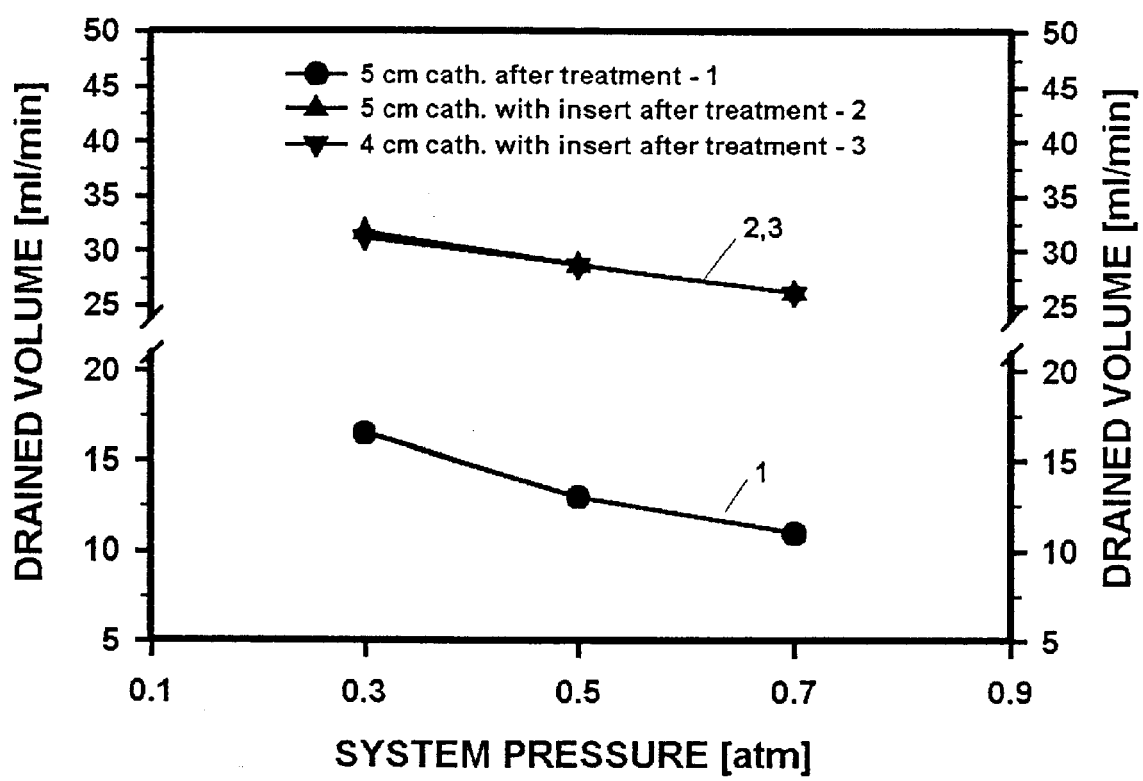
FIG. 13 is a graph illustrating the drained volume (ml/min) for catheters configured with and without inserts for various fluid pressures inside the catheter.

FIG. 13 illustrates drainage volumes for catheters for various conditions, both with and without an insert and when exposed to different operating pressures inside the closed loop system (on the order of 0.3, 0.5, and 0.7 atm). For this analysis, a thermal ablation treatment temperature of 62° C. (the temperature of the liquid at the entry to the inlet lumen 26$i$) was employed for a 45-minute treatment period. During operation, as the catheter is exposed to the thermal treatment temperatures, the lumens can change size (here the enlargement of the "in" and "out" lumens cause the drainage lumen to decrease in size) which may be attributed to PVC relaxation (the material of the lumens and shaft outer wall in this analysis). This can, in turn, reduce the drainage volume significantly from the designed drainage volume (which is typically about 20–30 ml).

When additional pressure is put into the system (such as by adding additional fluid volumes or exposing to swollen or inflamed tissue), a decrease in drainage volume may occur. This indicates that the pressure may cause the inner drainage lumen to collapse (or at least partially close). Notably, in situations where the insertion tube or insert was used, all drained volumes were significantly larger than that seen in conventional catheters after thermal treatments and approach the designed drainage volumes.

The insert 80 can provide improved drainage flow volumes (a larger drainage path) through the drainage channel 28 in the catheter 20 after thermal treatments such as thermal ablation and/or after other therapies (such as surgery or the like where tissue is disturbed and edema or swollen tissue can result). In addition, the increased stiffness or rigidity of the drainage path 28 can redistribute the heat and pressure delivered by the treatment balloon 23 such that it is redirected from the drainage lumen 28 toward the outer wall 30 or zone of the catheter 20. That is, the increased structural integrity of the drainage lumen 28 alters the shape of the inlet and outlet circulation lumens 26$i$, 26$o$.

It should also be noted that, as an alternative to the use of an insert 80, or in combination therewith, the wall structure or thickness of the drainage lumen can be increased (such as to about 0.4–1.0 mm) and/or the drainage wall material can be configured from a material with an increased stiffness over the flexible lumen material. Still further, shaft configurations such as shown in FIGS. 4A–4G or certain of the designs shown in the embodiments of FIG. 3 can provide the desired increased structural rigidity which can inhibit closure of the drainage channel. Each of these solutions, alone or in combination, may provide increased drainage volumes over conventional catheters and particularly for thermal ablation treatment catheters.

The catheter 20 may also be configured with radiopaque markers 77 (FIG. 11A) to help identify the position in situ for X-ray visualization. As such, X-rays can be taken at insertion/placement (initial positioning) to confirm proper positioning of the catheter 20 in the subject in situ. It is preferred that, as shown in FIG. 11A, the radiopaque markers 77 be circumferentially arranged to extend about the entire circumference of the shaft of the catheter 20, both above and below the treatment balloon 23, so that the balloon 23 can be more readily accentuated and confirmed in the X-ray as located in the proper position in the prostate, above the sphincter. Alternatively, or in addition, one or more longitudinally extending radiopaque markers 77$x$ can be arranged to extend substantially along a length of the catheter at various radial positions. The longitudinal markers can be arranged as at least 4 markers symmetrically separated and aligned about the cross-sectional width of the catheter, typically at 90-degree radial separation to allow for X-ray identification irrespective of the image angle.

The radiopaque markers are applied to block the transmission of X-ray for better contrast in images. The opacity, degree of contrast, and sharpness of the image may vary with material and type of process used to create the marker. The radiopaque marker(s) may be arranged on the catheter by any suitable biocompatible marker technique such as non-toxic radiopaque coatings, inks, thin-films, paints, tapes, strips, shrink tubing, and the like. See e.g., Richard Sahagian, *Critical Insight: Marking Devices with Radiopaque Coatings*, Medical Device & Diagnostic Industry (May, 1999), also available at URL devicelink.com/mddi/archive/99/05/011. Other examples of radiopaque markers include polyolefin inks available as No-Tox® Medical Device Polyolefin Inks from Colorcon, custom coatings for radiopacity from Hydromer Inc, of Branchburg, N.J., and resin compounds with barium sulfate and/or bismuth, such as one available from New England Urethane Inc. of North Haven, Conn. See also Danilychev et al., *Improving Adhesion Characteristics of Wire Insulation Surfaces*, Wire Technology International, March 1994 (discussing various treatments such as gas plasma treatment systems for medical products) which may be appropriate for use in the fabrication of the treatment catheter 20.

As the catheters 20 of the present invention can reside in the body for typically between 12–72 hours (and potentially even longer), surface or other treatments or coatings may also be applied to, or integrated into or onto, the catheter 20 to achieve one or more of increased lubricity, low coefficient of friction (each for easier insertion) as well as increased tissue biocompatibility, such as resistance to microbial growth and/or configured to reduce the incidence of UTI and/or to promote healing and/or inhibit scarring.

In certain embodiments, the catheter 20 comprises a biocompatible protective coating which may include an anti-microbial or biostatic material, at least on its exposed surfaces (those that contact the body and/or the exposed surfaces of one or more of the inner fluid lumens). The biocompatible coating can inhibit the growth of undesirable microbial organisms such as bacteria, yeast, mold, and fungus while the catheter 20 is held in the body during the initial healing period as noted herein. The protective coating can be provided by adding a conformal coating onto the desired shaft material such as a coating process which exposes the desired catheter surfaces to a gas-phase manomer of Parylene at low pressure (this type of coating process can be particularly suitable for silicone), such as is available from Parylene Coating Services, Inc. located in Katy, Tex.

The biocompatible biostatic or antimicrobial material can be chemically bound to the catheter such that it has a substantially non-leachable formulation or as a controlled time release agent so as to inhibit the formation of biofilms on the catheter and to inhibit or reduce infections caused by leaving the catheter 20 in the body for an extended period. The biocompatible coating can also be configured with anti-thrombogenic or anti-restenosis agents within the coating itself so as to generate a timed or slow release of same.

One suitable material may be the antimicrobial silver zeolite-based product available from HealthShield Technologies LLC of Wakefield, Mass. Another alternative is a Photolink® Infection Resistance antimicrobial coating or a hemocompatible coating from SurModics, Inc. of Eden Prairie, Minn. The coating may also include other bioactive ingredients (with or without the antimicrobial coating), such as antibiotics, and the like, as will be discussed further below.

In other embodiments, fluids can be delivered locally, such as through the catheter 20 to the treated region. These fluids can be a number of different types and can be used to cleanse, deliver medicines to treat infections, promote healing, reduce scarring and the like. For example, fluids can be directed through the catheter drainage channel 28 and out into the body of the subject to cleanse the treated region after (and/or before or during) treatment to reduce the pathogen agents from the urinary tract and promote healing. For example, chlorhexidine gluconate (commercially known as HIBICLENS), povidone iodine (BETADINE), and sodium hypochlorite (CLOROX) can be delivered locally through the catheter positioned in the body of the subject. In addition, or alternatively, proteolytic enzymes (such as TRAVASE available from Boats Pharmaceuticals in Lincolnshire, IUL) can be directed to the treated region which may help digest necrotic soft tissue, which, in turn, may also help reduce the healing period and/or promote healing.

In other embodiments, fluids can be delivered locally to inhibit scar formation and/or to promote healing during the post treatment period. One such product which may be suitable for wound healing (including wounds caused by burns) is a hydrogel solution, is available from FibroGen, Inc., located in San Francisco, Calif. Another hydrogel substance is extracted from the Aloe Vera L. plant. One commercially available product is identified as ULTREX, produced by Carrington Laboratories located in Irving, Tex. The wound-healing product can moisturize the treated region and inhibit infection as well as promote faster healing rates. These substance can be delivered immediately subsequent to the thermal treatment and/or at various times over the healing period. The substances may also be incorporated onto desired surfaces of the catheter for automatic time release of the substances in situ.

Various prophylactic antibiotics can also be delivered systemically such as orally, before and/or after a thermal treatment or thermal ablation session. In other embodiments, antibiotics or anti-inflammatory (including non-steroidal and α-blockers, Cox-inhibitors, or antioxidants) or other selected drugs, can be delivered directly into the treatment region. For treatment regions which are in locations which expose them to body contaminants such as the prostate, this can result in reduced catheterization time and reduced incidence of urinary tract infections (UTI). Antibiotics known as RIFAMPIN, MINOCYCLINE, and VANCOMYCIN or others have been successfully used in certain medical or clinical sites. Non-steroidal anti-inflammatory drugs can also be used such as CELEBREX that has also been used in conjunction with WIT of the prostatic urethra (given before and/or after the thermal ablation treatment). NITROFURATOIN (trade name MACRODANTIN) has been incorporated into the catheter itself to treat UTI and to promote faster healing. Alpha-blockers such as FLOMAX, CARDURA, and HYTRIN have also been used, as well as other agents such as DETROL, DITROPAN XL, and PYRIDIUM.

Examples of other anti-inflammatory medicines which may be used either locally and/or systemically with thermal treatments and thermal ablation therapies include, but are not limited to, steroids, nonsteroidal anti-inflammatory drugs such as TOLMETIN (trade name TOLECTIN), MECLOFENAMATE (trade name LEFLUNOMIDE), MECLOFENAMATE (trade name MECLOMEN), MEFENAMIC ACID (trade name PONSTEL), DICLOFENAC (trade name VOLTAREN), DICLOFENAC POTASSIUM (trade name CATAFLAM), NABUMETONE (trade name RELAFEN), DIFLUNISAL (trade name DOLOBID), FENOPROFEN (trade name NALFON), ETODOLAC (trade name LODINE), KETOROLAC (trade name TORADOL) and other anti-inflammatory drugs such as LEFLUNOMIDE, ROFECOXIB (trade name VIOXX), IBUPROFIN (such as MOTRIN) and CELECOXIB (trade name CELEBREX). Other types of medicines or drugs can also be used such as anti-hypertensive drugs including TERAZOSIN (trade name HYTRIN), DOXAZOSIN (trade name CARDURA), and immunosuppressive drugs including CYCLOSPORINE (trade name SANDIMMUNE or NEORAL).

Additional examples of antibiotics which may be suitable for use in conjunction with thermal treatments including thermal ablations, include, but are not limited to, CIPRO, LEVAQUIN, SEPTRA, GENTAMYCIN, CLINDAMYCIN (trade name CLEOCIN), AZITHROMYCIN (trade name ZITHROMAX), TRIMETHOPRIM (trade name TRIMPEX or PROLOPRIM), NORFLOXACIN (trade name NOROXIN).

In addition, or alternatively, the catheter 20 may be configured with a biocompatible lubricant or low-friction coating material (at least along selected regions so as not to interfere with the heat transmissivity at the treatment balloon) to help reduce any discomfort associated with the insertion of the device into the body. Coatings which may be appropriate include coatings which promote lubricity and wettability. The coatings may be provided such that the hydrophilic state is transient or more permanent. Conventional processes such as plasma, corona, or ozone processing are thought to have a transient hydrophilic state. In contrast, a stable long term hydrophilic state may be provided by the use of HydroLAST™ from AST which proposes a submicron coating to alter a hydrophobic substrate into a long term or permanent hydrophilic substrate.

The hydrophilic coating can be applied as a thin layer (on the order of about 0.5–50 microns thick) which is chemically bonded with UV light over selected external surfaces of the catheter 20 (such as proximate the distal end and along the shaft 25). One such product is a hydrophilic polymer identified as Hydrolenet® available from SurModics, Inc., of Eden Prairie, Minn. Other similar products are also available from the same source. Another suitable product may be HydroLAST™ from AST which proposes a submicron coating to alter a hydrophobic substrate into a long term or permanent hydrophilic substrate.

Still further, the catheter 20 may be configured to provide both the lubricious coating and bioactive ingredients which can be configured to provide sustained or time release matrices of antibiotics, antimicrobial, and anti-restenosis agents, identified as LubrilLast™ from AST as noted above. Another product which may be suitable are medical hydrogels such as identified by the name of Aquatrix™II, available from Hydromer, Inc. located in Branchburg, N.J. Examples of products which can provide one or more of microbial resistance, wet lubricity, biocompatibility, and drug delivery include coatings such as LubriLAST™, a lubricious coating, available from AST of Billerica, Mass., and coatings available from Hydromer Specialty Coatings (this company also provides a non-leaching radio-opaque polymeric coating). These coatings may be formulated as a matrix onto selected surfaces of the catheter body to provide a timed-release dispersion of the desired treatment (such as drug delivery) into the body (i.e., "biodegradable or bioabsorbable coatings").

In each of the embodiments described herein, the catheter and coatings are preferably configured to withstand suitable sterilization processes as they will be used in medical applications.

In certain embodiments of the present invention, at a desired time, typically post-treatment, the catheter 20 may be configured to deliver biodegradable materials as flowable fluids through the drainage channel 28 or through the inlet channel 26i to the treatment balloon to emit through the treatment balloon 23 onto the treated tissue or targeted region. Alternatively, flowable fluids can be dispersed into the targeted region after the treatment catheter 20 is removed. In any event, these flowable fluids or solutions, when subjected to different conditions, harden or solidify to form a localized shell which can provide a biodegradable stent for the treated region. For example, polymerizing gels that solidify upon contact with body fluids can be inserted into the subject to the treated region. In operation, these gels can flow about the catheter body and form in situ, a protective shell or coating about the targeted region. The biodegradable materials can also be a combination of two polymers that solidify when they come into contact with each other. In this way, a biodegradable stent may be used without requiring the use of a conventional indwelling catheter or stent, in a way which may provide adequate urinary passage openings. For additional description of biodegradeable stents, see concurrently filed co-pending and co-assigned U.S. patent application Ser. No. 10/011,494 TBD, entitled "Biodegradeable Stents", the contents of which are hereby incorporated by reference as if recited in full herein.

Typical bio-absorbable materials used in urology include high molecular weight polymers of polylactic or polyglycolic acid. Some of these materials are thought to have been used in Finland after laser ablation treatment of the prostate as well as after trans-urethral microwave therapy, and for recurrent bulbous urethral strictures. See Isoltalo et al., *Biocompatibility testing of a new bioabsorbable X-ray positive SR-PLA 96/4 urethral stent*, Jnl. Of Urol., pp. 1764–1767, Vol. 162 (1999). Some of the bio-absorbable materials or gels may also be used as drug delivery systems after thermocoagulation treatments. Examples of companies in the United States that may be developing or have materials which may be suitable to act as biodegradable or bioabsorbable stents include: MedLogic Global Corporation, located in Colorado Springs, Colo. (proposing hydrogel polymers which solidify at high temperatures after they are injected in liquid form); Surgical Sealants, Inc., located in Woburn, Mass. (proposing THOREX, an albumin base polymer which can purportedly adhere to tissue in less than about 15 seconds); FibroGen, Inc., located in So. San Francisco, Calif. (proposing recombinant collagens, human proteins which provide may reduce immune reactions or transfer of pathogens from animal-based materials); Biosyntech Canada, located in Laval, Quebec (proposing BST-GEL which is in a liquid state at low temperature and at a solid state at body temperature and which may be used for drug release); Cohesion Technologies located in Palo Alto, Calif. (proposing COSEAL, a synthetic self-polymerizing gel, which is a mixture of collagen and polyethylene glycol allegedly resorbable within 30 days and capable of drug delivery); and Atrix located in Ft. Collins, Colo. (proposing ATRIGEL, a biodegradable polymer system which can be applied to tissue as a liquid which then solidifies upon contact with the body's moist environment and which has the ability to time-release different drugs).

FIG. 14 is a block diagram of a method of fabricating an elongated catheter with insulated portions. The catheter has an outer wall which is configured to encase at least one fluid lumen therein. As shown, a quantity of liquid insulation mixture is introduced into a desired region of the catheter such that the liquid insulation mixture resides intermediate the outer wall and the at least one fluid lumen (Block 400). The liquid is then allowed to harden to define at least one thermally insulated region to inhibit the thermal transfer of heat from the at least one fluid lumen through the outer wall of the catheter (Block 410). The change in physical state can be induced by time, temperature (heat), or exposure to UV light. In a preferred embodiment, the liquid insulation mixture comprises a thermoset material, which can be liquid polyurethane, along with hollow plastic microspheres. The catheter can include a plurality of air lumens, channels, or segments with void spaces, positioned between the outer wall and the at least one fluid lumen, and that the introducing step can be carried out by directing the liquid mixture into all or portions of the void spaces.

FIG. 15 is a block diagram of a method for inhibiting the closure of a fluid lumen or channel held in a flexible treatment catheter having at least one fluid lumen therein during or after exposure to a therapeutic treatment which can include surgery and thermal treatments such as those employing elevated or thermal ablation temperatures. The method includes the step of configuring and sizing the catheter such that it can be inserted into a body lumen, the catheter having at least one internally located fluid channel associated therewith (Block 500). The method further includes the step of positioning an elongated insert into a selected one of the at least one fluid channel such that the insert inhibits the closure of the fluid channel when the catheter is held in position in the subject during and/or after exposure to the applied treatment (Block 510). Preferably, the insert is configured to withstand pressures associated with edema or swelling as the body reacts to the localized treatment to maintain an opening of a desired size for fluids to travel therethrough. The insert can be configured to inhibit closure of the selected fluid channel after exposure to temperatures above about 40° C., and typically above about 45° C., for a duration of over 5–30 minutes so that it can still provide a sufficient fluid channel size to allow fluid drainage therethrough. In certain embodiments, the insert can be configured to allow sufficient drainage even when held in the body for a period of at least about 12–72 hours after the delivery of thermal ablation therapy.

Figure 16:
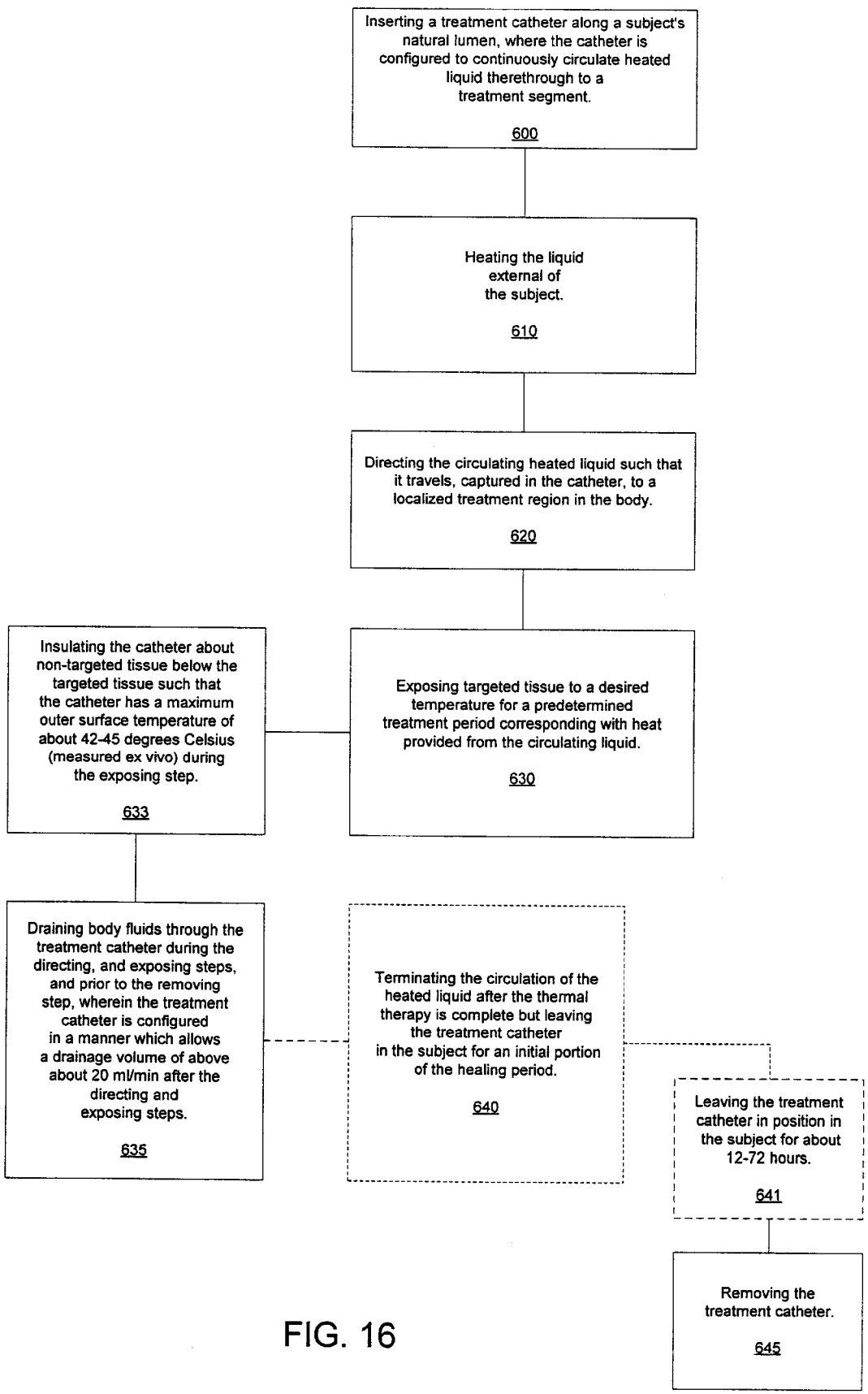
FIG. 16 is a block diagram of a method for treating conditions of the prostate according to embodiments of the present invention.

FIG. 16 is a block diagram of a method for treating a region in the natural lumen or body cavity of a subject. The method includes inserting a flexible treatment catheter configured to circulate heated liquid into desired region of the subject (Block 600) and heating liquid to a desired treatment temperature external of the body (Block 610). For some embodiments, such as for treating prostatitis, the liquid can be heated to between about 40–47° C. In other embodiments, such as for thermal ablation applications, the circulating heated liquid can heated to a temperature between about 45–80° C. The circulating heated liquid is directed through the catheter to a treatment balloon such that it travels, captured in the catheter, to a localized treatment region in the body of the subject (Block 620). The tissue in the localized treatment region is exposed to a desired temperature for a predetermined treatment period by exposure to the heated circulating liquid (Block 630). The method also includes the step of insulating the non-targeted tissue below the targeted tissue in the treatment region such that the non-targeted tissue positioned there is exposed to a maximum temperature of about 45–45° C., and in particular embodiments below about 42° C., from contact with the treatment catheter during the exposing step (Block 633).

Additionally, body fluids are directed to drain through the treatment catheter during the directing, exposing, and leaving steps, and the treatment catheter is configured in a manner that allows a drainage volume of above about 20 ml/min (preferably above about 25 ml/min.) after the directing and exposing steps (Block 635). In any event, after the thermal therapy is completed, circulation of the heated liquid can be terminated (Block 640). The treatment catheter can be left in position in the subject for an initial portion of the healing process (the initial portion including about the first 12–72 hours, and more preferably about 24–48 hours) (Block 641). This delay in removal of the treatment catheter (Block 645) can reduce the likelihood or amount of bleeding and subsequent blood clotting caused by premature removal of the treatment catheter and/or help mold the tissue in the treatment region. A post-treatment tissue-molding stent can be inserted as desired subsequent to and proximate in time to removal of the treatment catheter.

The method may be used to treat BPH or prostatitis, or other prostate, urinary, or body condition. For prostatic BPH applications, the liquid can be heated external of the body to a temperature in the range of between about 57°–62° C. or greater. The circulating heated liquid is directed through the catheter to a treatment balloon such that it travels, captured in the catheter, through the penile meatus, along the penile urethra, the bulbous urethra, and the membranous urethra to a localized treatment region in the prostate. The tissue in the localized treatment region in the prostate is exposed to a temperature above about 45° C. for a predetermined thermal ablation treatment period by exposure to the heated circulating liquid (typically input at or above about 60° C. for more than about 30 minutes). As noted above, the localized treatment region can be an upper portion of the urethra from the prostate (the prostatic urethra) leaving the lower portion of the urethra from the prostate (the membranous urethra) non-ablated.

This can be accomplished in circulating systems (which heat remotely) by insulating the shaft of the treatment catheter up to the treatment balloon to inhibit the exposure of non-targeted tissue to ablation temperatures. The method also includes the step of insulating the non-targeted tissue below the prostate in the urethra such that the non-targeted tissue positioned there is exposed to a maximum temperature of about 42–45° C., and in certain embodiments at or below about 42° C., from contact with the treatment catheter during the directing and exposing steps (when measured ex vivo on bench tests). Additionally, urine is directed to drain through the treatment catheter during the directing, exposing, and leaving steps, and the treatment catheter is configured in a manner that allows a drainage volume of above about 20 ml/min (preferably above about 25 ml/min.) after the directing and exposing steps.

In other embodiments, such as for dysfunctional uterine bleeding, the liquid may be heated above 62° C., such as to about 70–80° C., or even higher. In these embodiments, the increased insulation can be configured so that the non-targeted tissue is also exposed to a maximum temperature of below about 42–45° C., and in certain embodiments to a maximum temperature that is at or below about 42° C.

As noted above, the treatment catheter can be left in position in the subject for an initial portion of the healing process (the initial portion including about the first 12–72 hours, and more preferably about 24–48 hours). This delay in removal of the treatment catheter can reduce the likelihood or amount of bleeding and subsequent blood clotting caused by premature removal of the treatment catheter. The treatment balloon can be left inflated and even inflated further to facilitate shaping or molding the treated tissue as the tissue reacts to the treatment (swelling, edema, etc). In certain embodiments, where the natural healing process is such that the urinary passage may be restricted during healing, a post-treatment tissue-molding stent can be inserted into or formed about the prostatic urethra subsequent to and proximate in time to removal of the treatment catheter. The stent can be biodegradable or non-biodegradable. The stent as well as the catheter can include medications and other surface treatments as discussed above.

It will be understood that one or more blocks of the block diagrams and combinations of blocks in block diagram figures can be implemented or directed to be carried out by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus or associated hardware equipment to function in a particular manner diagrams.

The invention will now be illustrated with reference to certain examples which are included herein for the purposes of illustration only, and which are not intended to be limiting of the invention.

EXAMPLES

Figure 5A:
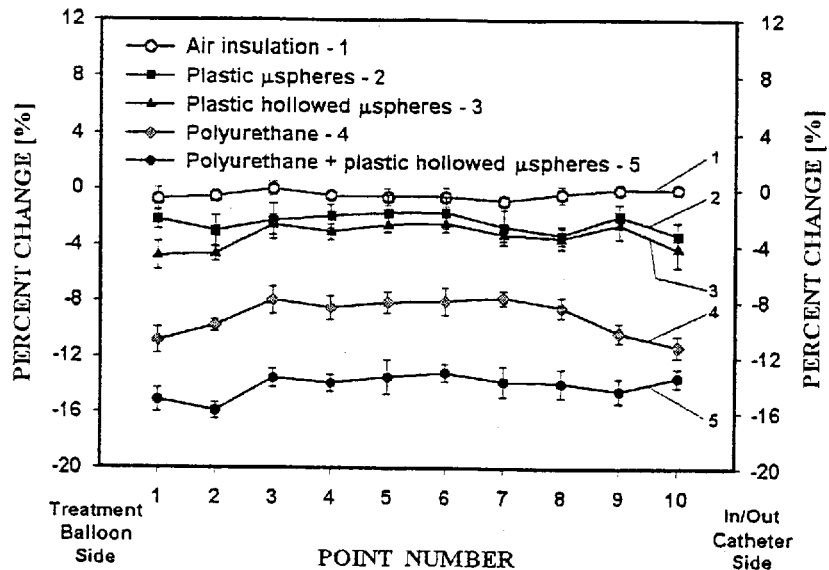
FIG. 5A is a graph illustrating the temperature distribution of a catheter shaft (as percent change from the temperature exhibited with air insulation). The temperatures were measured ex vivo at 10 different incremental points (spaced apart about one inch) along the catheter shaft. Temperature measurements were taken at four (90 degree) intervals about the exterior surface of the shaft at each of the 10 different positions to determine where the highest temperatures were located. For each of the 10 different positions (indicated as numbers 1–10 on the bottom of the graph), a plurality of temperature measurements were taken during different time periods within one or more 45 minute thermal ablation treatment periods. The lines on the graph illustrate the mean (the center point) and standard deviation (the upper and lower bars about the center point) of the temperatures measured at each of the 10 points. Each line on the graph represents the results for one of five different insulation material types or mixtures. The temperatures shown correspond to the location on the shaft where the maximum temperatures were measured ex vivo in a laboratory set-up along the shaft as the shaft was exposed to heated circulating fluid. The heated circulating fluids had an input temperature condition set to about 60° C. during a thermal treatment session lasting about 45 minutes. The lowest line in the graph corresponds to the lowest measured temperatures and the most thermal insulation as tested.
Figure 5B:
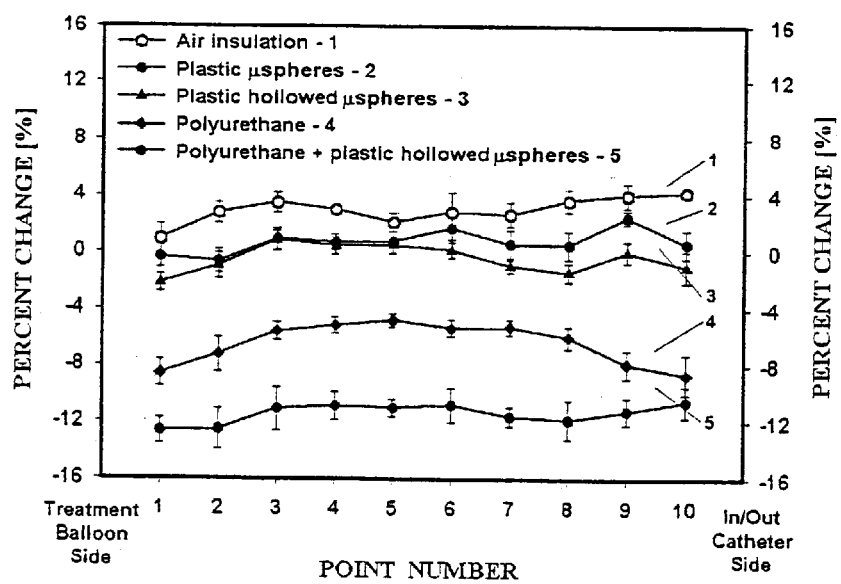
FIG. 5B is a graph similar to FIG. 5A illustrating the temperature distribution for a shaft enclosing circulating fluid heated to an input condition of about 62° C.

FIGS. 5A and 5B illustrate the temperatures along the shaft 25 for a catheter shaft configured similar to that shown in FIG. 3D during bench experiments conducted on same. For the measurements, only the material inserted into the tubes 34 was altered (so that the outer wall thickness and the inner wall thickness and quantity of individual conduits the same for comparison purposes). It should be noted, however, that the present invention is not limited to the structural configurations illustrated in the figures. For example, the number of partitions, tubes, baffles, and structural configurations of the wall segments shown in the figures may vary in number and size/shape and still provide adequate insulation according to the present invention.

Referring again to FIGS. 5A and 5B, the plot of air insulation temperature (line 1) corresponds to catheters with conventional insulation which is provided by a series of circumferentially arranged, enclosed air-lumens or conduits which surround the inlet and outlet fluid circulating channels 26i, 26o and the urinary drainage channel 28. These air conduits were filled with different materials to test their ability to provide adequate insulation at a 60° C. setting (fluid temperature inlet condition) as shown in FIG. 5A and for a 62° C. setting (fluid temperature inlet condition) as shown in FIG. 5B. The tested insulation materials shown in these graphs are air (line 1), plastic microspheres (line 2), hollow plastic microspheres (line 3), polyurethane (line 4), and a mixture of polyurethane and hollow plastic microspheres (line 5). At both operating temperatures, all of the filling materials performed better than air alone. However, polyurethane alone, and polyurethane mixed with hollow plastic microspheres provided the most effective insulation. Indeed, the polyurethane/plastic microspheres mixture provided an average reduction of about 12–14% in catheter shaft temperature as compared to air-filled lumens.

Figure 6A:
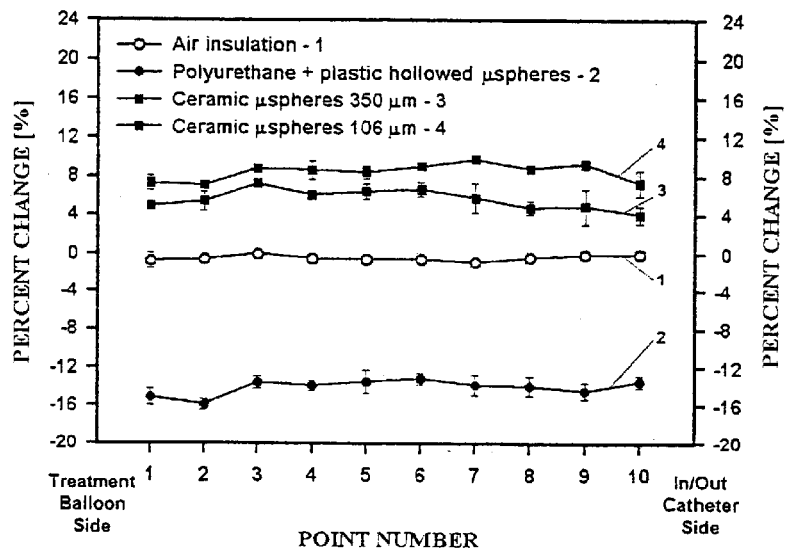
FIGS. 6A and 6B are graphs similar to FIGS. 5A and 5B illustrating the temperature distribution (as a percent change from the air insulation) for a different selection of insulation materials.
Figure 6B:
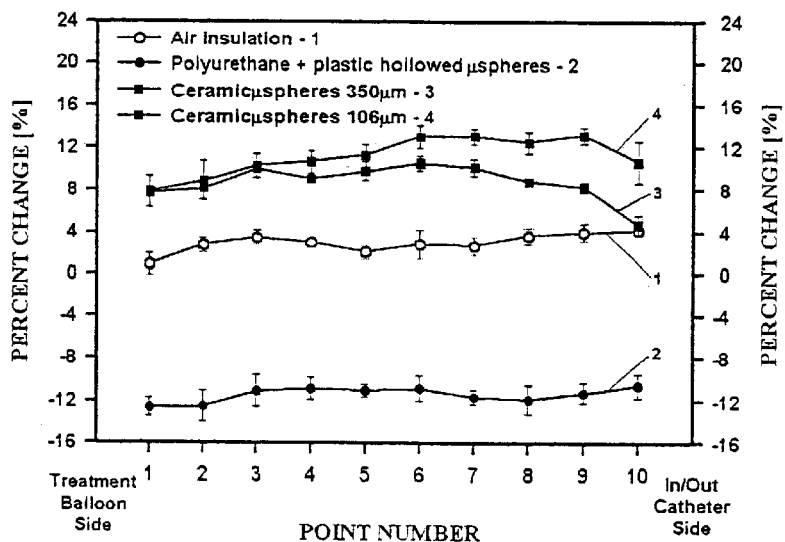

Referring now to FIGS. 6A and 6B, these graphs plot shaft outer surface temperatures for catheters insulated with an air (line 1), polyurethane and hollow plastic microspheres (line 2), ceramic microspheres sized at about 360 μm (line 3), and ceramic microspheres sized at about 106 μm (line 4). Notably, the ceramic microspheres (lines 3 and 4) provided increased thermal transmissivity and enhanced heating (of about 5–12%) as measured on the outer surface of the catheter shaft over the conventional air lumens alone. Again, however, the polyurethane and hollow plastic microspheres insulation material mixture provided the most effective (reduced temperature) thermal insulation under these test conditions.

Although described herein primarily for use as a prostatic thermal treatment catheter, it will be appreciated by those of skill in the art that the insulation configurations of the instant invention as well as the lumen insert of the instant invention may be applied to other catheter configurations and other applications for catheters adapted for insertion into natural lumens or body cavities such as blood vessels (including, but not limited to, arteries), the rectum, the colon, the uterus, the throat, the ear, the nose, passages of the heart and/or associated valves, the respiratory system, and the like.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A treatment catheter configured for insertion into a body cavity or lumen of a biological subject, said treatment catheter comprising:

a flexible elongated tubular body having an outer wall with an external surface and at least one fluid lumen axially extending therein, wherein said tubular body comprises a region having increased thermal insulation relative to another region thereof, said increased thermal insulation region configured to encase said at least one fluid lumen therein, said at least one fluid lumen extending a length along said tubular body, wherein said increased thermal insulation region comprises a liquid elastomeric material which is introduced into said catheter such that it is captured between said outer wall and said at least one fluid lumen and then solidified therein prior to use.

2. A treatment catheter according to claim 1, wherein said increased thermal insulation region is defined by said outer wall, a plurality of void spaces interposed between said outer wall and the inner wall of said at least one fluid lumen, and wherein said liquid elastomeric material is introduced into selected ones of said void spaces.

3. A treatment catheter according to claim 2, wherein at least one of said void spaces has a perimeter with a polygonal shape.

4. A treatment catheter according to claim 3, wherein at least one of said void space perimeters has a substantially triangulated shape.

5. A treatment catheter according to claim 2, wherein at least one of said void spaces has a perimeter with a substantially circular shape.

6. A treatment catheter according to claim 2, wherein at least one of said void spaces has a perimeter with a substantially oval shape.

7. A treatment catheter according to claim 1, wherein said liquid elastomeric material comprises hollow microspheres.

8. A treatment catheter according to claim 7, wherein said insulating material comprises at least 10% volume of hollow microspheres.

9. A treatment catheter according to claim 7, wherein said hollow microspheres are hollow plastic microspheres, and wherein said liquid elastomeric material comprises at least one of nylon, polyurethane, polyethylene, silicone.

10. A treatment catheter according to claim 1, wherein said liquid elastomeric material comprises polyurethane.

11. A treatment catheter according to claim 1, further comprising an inflatable treatment balloon positioned about a peripheral distal portion of said elongated tubular body such that said treatment balloon is expandable to a configuration which extends radially outward a distance from said outer wall external surface of said tubular body, wherein said at least one fluid lumen is a plurality of lumens all axially extending within said tubular body such that said plurality of lumens are encased by said outer wall and, for at least a portion of the length of a more proximal portion of said tubular body relative to said treatment balloon, said plurality of fluid lumens are encased by outer wall and said increased thermal insulation region, wherein said plurality of lumens include a circulating fluid inlet lumen, a circulating fluid outlet lumen, and a drainage and fluid delivery lumen, and wherein said fluid inlet and outlet lumens are in fluid communication with said treatment balloon and are configured, in operation, to cause said treatment balloon to expand.

12. A treatment catheter according to claim 11, wherein, in position in a subject, said treatment catheter is configured to circulate a liquid heated external of said tubular body through said inlet lumen to said treatment balloon and out through said outlet lumen, the liquid heated to a temperature sufficient to thermally treat or ablate tissue at a desired biological target site proximate said treatment balloon, and wherein, in operation, said outer surface of said outer wall in said increased thermal insulation region has a temperature which is at or below about 45° C.

13. A treatment catheter according to claim 12, wherein the temperature of the heated circulating liquid as it enters said inlet lumen of said tubular body is at or greater than about 60° C., and wherein, measured ex vivo, said external surface of said outer wall about said increased thermal insulation region exhibits a maximum average temperature of about 42–45° C. after a thermal treatment period of at least 30 minutes.

14. A treatment catheter according to claim 13, wherein said drainage and delivery lumen is centrally disposed within said tubular body, and wherein said inlet and outlet lumens are positioned on opposing sides thereof.

15. A treatment catheter according to claim 12, wherein said treatment catheter is sized and configured for insertion into the urethra of a male subject, the urethra generally including, in serial order from the external most portion to the internal portion, the penile meatus, the penile urethra, the bulbous urethra, the sphincter, the membranous urethra, the prostatic urethra, the bladder neck and the bladder, wherein said tubular body is sufficiently conformable to yield to the contours of the subject's body as it is inserted therein, yet sufficiently rigid to maintain said drainage and delivery lumen in an open condition sufficient to discharge urine at a flow rate of at least about 20 ml/min when said catheter is in position in the urethra and exposed to prostatic tissue which is exhibiting distress during or subsequent to undergoing a thermal ablation therapy.

16. A treatment catheter according to claim 15, further comprising a anchoring balloon positioned on a distal portion of said tubular body such that it is more distal than said treatment balloon, said anchoring balloon configured and sized such that, when inflated and in position in the biological subject, said anchoring balloon resides against the bladder neck of the subject to position said treatment balloon in the prostate relative to the bladder of the subject, wherein said treatment catheter includes a port on said distal portion thereof in fluid communication with said drainage and delivery lumen to allow urine to drain therethrough.

17. A treatment catheter according to claim 1, wherein said at least one fluid lumen comprises at least one drainage and fluid delivery lumen, and wherein said tubular body is sufficiently conformable to yield to the contours of the subject's body as it is inserted therein, yet sufficiently rigid to maintain said drainage and delivery lumen in an open condition which is sized at about at least 50–75% of the size of the lumen outside the body before the treatment, when in position in the body and exposed to tissue which is exhibiting distress during or subsequent to a treatment.

18. A treatment catheter according to claim 1, wherein said at least one fluid lumen comprises three lumens, a circulating inlet channel, a circulating outlet channel, and at least one drainage lumen, wherein in cross-section, said three lumens define three substantially equal pie shaped areas extending radially outward from a common center, and wherein said tubular body is sufficiently conformable to yield to the contours of the subject's body as it is inserted therein.

19. A treatment catheter according to claim 1, wherein said at least one fluid lumen comprises four lumens, a circulating inlet channel, a circulating outlet channel, and two drainage lumens, wherein in cross-section, said four lumens each occupy a quadrant of a common circle, and wherein said tubular body is sufficiently conformable to yield to the contours of the subject's body as it is inserted therein.

20. A treatment catheter according to claim 1, wherein said at least one fluid lumen includes at least one drainage and fluid delivery lumen with a flexibly configured elastomeric wall, and said catheter further comprises an elongated insert disposed in said drainage and delivery lumen to provide increased structural rigidity to said lumen wall inhibit the collapse of said drainage and delivery lumen when positioned in the subject and exposed to the body's reaction to a therapeutic treatment.

21. A treatment catheter according to claim 1, wherein said treatment balloon comprises a thin wall expandable elastomeric balloon comprising a surface coating comprising ceramic microspheres positioned thereon to enhance the thermal transmissivity of said treatment balloon.

* * * * *